(12) United States Patent
Cheatham, III et al.

(10) Patent No.: US 9,687,404 B2
(45) Date of Patent: Jun. 27, 2017

(54) GARMENT SYSTEM INCLUDING AT LEAST ONE MUSCLE OR JOINT ACTIVITY SENSOR AND AT LEAST ONE ACTUATOR RESPONSIVE TO THE SENSOR AND RELATED METHODS

(71) Applicant: Elwha LLC, Bellevue, WA (US)

(72) Inventors: Jesse R. Cheatham, III, Seattle, WA (US); Roderick A. Hyde, Redmond, WA (US); Muriel Y. Ishikawa, Livermore, CA (US); Jordin T. Kare, Seattle, WA (US); Eric C. Leuthardt, St. Louis, MO (US); Nathan P. Myhrvold, Medina, WA (US); Elizabeth A. Sweeney, Seattle, WA (US); Clarence T. Tegreene, Mercer Island, WA (US); Charles Whitmer, North Bend, WA (US); Lowell L. Wood, Jr., Bellevue, WA (US); Victoria Y. H. Wood, Livermore, CA (US)

(73) Assignee: ELWHA LLC, Bellevue, WA (US)

( * ) Notice: Subject to any disclaimer, the term of this patent is extended or adjusted under 35 U.S.C. 154(b) by 273 days.

(21) Appl. No.: 14/469,169

(22) Filed: Aug. 26, 2014

(65) Prior Publication Data
US 2016/0058644 A1    Mar. 3, 2016

(51) Int. Cl.
*A61H 23/02*   (2006.01)
*A61H 1/00*    (2006.01)

(52) U.S. Cl.
CPC ..... *A61H 1/008* (2013.01); *A61H 2201/1207* (2013.01); *A61H 2201/1238* (2013.01);
(Continued)

(58) Field of Classification Search
CPC .......... A61H 7/00; A61H 7/007; A61H 7/008; A61H 9/00; A61H 9/0157; A61H 9/02;
(Continued)

(56) References Cited

U.S. PATENT DOCUMENTS

| | | |
|---|---|---|
| 5,218,954 A | 6/1993 | van Bemmelen |
| 5,396,896 A | 3/1995 | Tumey et al. |

(Continued)

FOREIGN PATENT DOCUMENTS

| | | |
|---|---|---|
| CA | 2332747 | 4/2001 |
| WO | WO 2014/041032 | 3/2014 |

OTHER PUBLICATIONS

PCT International Search Report; International App. No. PCT/US2015/057954; Feb. 4, 2016; pp. 1-4.
(Continued)

*Primary Examiner* — Steven Douglas
(74) *Attorney, Agent, or Firm* — Dorsey & Whitney LLP

(57) ABSTRACT

Embodiments described herein relate to a garment system including at least one muscle or at least one joint activity sensor, and at least one actuator that operates responsive to sensing feedback from the at least one muscle or the at least one joint activity sensor to cause a flexible compression garment to selectively compress against or selectively relieve compression against at least one body part of a subject. Embodiments disclosed herein also relate to methods of using such garment systems.

50 Claims, 11 Drawing Sheets

(52) U.S. Cl.
CPC .. *A61H 2201/164* (2013.01); *A61H 2201/165* (2013.01); *A61H 2201/1635* (2013.01); *A61H 2201/5058* (2013.01); *A61H 2201/5097* (2013.01); *A61H 2230/207* (2013.01); *A61H 2230/50* (2013.01); *A61H 2230/60* (2013.01)

(58) Field of Classification Search
CPC ...... A61H 9/0207; A61H 9/0214; A61H 9/50; A61H 9/5058; A61H 9/5071; A61H 9/5074; A61H 9/5082; A61H 2230/50; A61H 2230/505; A61H 2201/00; A61H 2201/0157; A61H 2201/02; A61H 2201/0207; A61H 2201/0214; A61H 2201/50; A61H 2201/5058; A61H 2201/5071; A61H 2201/5074; A61H 2201/5082

See application file for complete search history.

(56) References Cited

U.S. PATENT DOCUMENTS

| | | | |
|---|---|---|---|
| 5,997,465 A | 12/1999 | Savage et al. | |
| 8,079,969 B2 | 12/2011 | Rousso et al. | |
| 8,734,369 B2* | 5/2014 | Perry .................. | A61H 9/0078 601/148 |
| 2003/0120183 A1 | 6/2003 | Simmons | |
| 2005/0154336 A1 | 7/2005 | Kloecker et al. | |
| 2006/0058694 A1 | 3/2006 | Clark et al. | |
| 2006/0122544 A1 | 6/2006 | Ciluffo | |
| 2007/0049853 A1 | 3/2007 | Adams et al. | |
| 2007/0265140 A1 | 11/2007 | Kim et al. | |
| 2008/0319359 A1 | 12/2008 | Moomiaie-Qajar et al. | |
| 2010/0056966 A1 | 3/2010 | Toth | |
| 2010/0305484 A1 | 12/2010 | Grollier et al. | |
| 2011/0066091 A1* | 3/2011 | Larson ............... | A61B 17/1325 601/134 |
| 2011/0092337 A1 | 4/2011 | Srinivasan et al. | |
| 2012/0065561 A1 | 3/2012 | Ballas et al. | |
| 2012/0071743 A1 | 3/2012 | Todorov et al. | |
| 2012/0089063 A1* | 4/2012 | Olson .................. | A61H 9/0078 601/152 |
| 2012/0130203 A1 | 5/2012 | Stergiou et al. | |
| 2012/0203132 A1 | 8/2012 | Blumensohn et al. | |
| 2013/0041235 A1 | 2/2013 | Rogers et al. | |
| 2013/0072301 A1 | 3/2013 | Mallinson | |
| 2013/0158444 A1 | 6/2013 | Herr et al. | |
| 2013/0289456 A1 | 10/2013 | Chang et al. | |
| 2013/0310719 A1 | 11/2013 | Davis et al. | |
| 2013/0345610 A1 | 12/2013 | Larson et al. | |
| 2014/0070957 A1 | 3/2014 | Longinotti-Buitoni et al. | |
| 2014/0135593 A1 | 5/2014 | Jayalth et al. | |
| 2014/0140567 A1 | 5/2014 | LeBoeuf et al. | |
| 2014/0142459 A1 | 5/2014 | Jayalth et al. | |
| 2014/0207036 A1 | 7/2014 | Perry et al. | |
| 2014/0276283 A1 | 9/2014 | Mansur, Jr. et al. | |
| 2014/0330186 A1 | 11/2014 | Hyde et al. | |
| 2015/0297437 A1* | 10/2015 | Neuenhahn .......... | A61B 5/4848 601/148 |

OTHER PUBLICATIONS

Vanhemert "Coming Soon: Workout Gear That Monitors Your Muscles" Dec. 4, 2013; Wired, 4 pages, http://www.wired.com/2013/12/these-smart-gym-clothes-are-the-future-of-wearable-computers/.

New Scale Technologies "Squiggle micro motor technology: Patented piezoelectric motor with small size, high force speed" Available as of Aug. 26, 2014, 3 pages. http://www.newscaletech.com/technology/squiggle-motors.php.

New Scale Technologies, Thomasnet.com "New Drive Solutions for Squiggle® Micro Motors Add Speed Control Options, Dynamic Optimization of Motor Performance over Temperature" Jul. 21, 2009, 2 pages. http://news.thomasnet.com/companystory/New-Drive-Solutions-for-SQUIGGLE-Micro-Motors-Add-Speed-Control-Options-Dynamic-Optimization-of-Motor-Performance-over-Temperature-828373.

Pi, www.pi.ws "Piezo Motor Solutions for Automation & Ultra-Precision Motion Control" Available as of Aug. 26, 2014, 4 pages. http://www.piezo-motor.net/piezo-motor_ultrasonic_and_ultra-precision_stepping.htm.

Pi, www.pi.ws "PILine Ultrasonic Piezomotor Working Principle" Available as of Aug. 26, 2014, 2 pages http://www.physikinstrumente.com/en/products/piezo_motor/piline.php.

Kim, et al. "Epidermal Electronics" Science 333, 838-843 (2011).

Hamaoka, et al. "The use of muscle near-infrared spectroscopy in sport, health and medical sciences: recent developments", Phil. Trans. R. Soc. A (2011) 369, 4591-4604.

Harrison, et al. "Portable acoustic myography—a realistic noninvasive method for assessment of muscle activity and coordination in human subjects in most home and sports settings" Physiological Reports, vol. 1, Issue 2: e00029, pp. 1-9 (2013).

Chen, et al. "A brief review of actuation at the micro-scale using electronics, electromagnetics and piezoelectric ultrasonics" Acoust. Sci. & Tech. 31, 2 (2010).

PCT International Search Report; International App. No. PCT/US2015/046717; Nov. 30, 2015; pp. 1-3.

* cited by examiner

GARMENT SYSTEM INCLUDING AT LEAST ONE MUSCLE OR JOINT ACTIVITY SENSOR AND AT LEAST ONE ACTUATOR RESPONSIVE TO THE SENSOR AND RELATED METHODS

BACKGROUND

Compression garments including clothing articles, such as socks, arm sleeves, leg sleeves, etc., can provide support to muscles of a body part on which the compression garments are worn. This support can be useful for people who have to stand for long periods, or people with circulation problems.

Compression sportswear, which is a specific type of compression garment, can also be worn by athletes during exercise. For example, bicycling shorts are a common type of compression sportswear. Compression sportswear can improve muscle functioning, and prevent chafing and rashes during and after exercise.

Compression garments are believed to have a number of positive effects on a user. For example, compression garments can help relieve pain from muscle stiffness and soreness, and reduce time taken for muscles to repair themselves. Also, when an appropriate amount of compression is used, compression garments can improve venous return and oxygenation to working muscles.

SUMMARY

Embodiments disclosed herein relate to a garment system including at least one muscle or at least one joint activity sensor, and at least one actuator that operates responsive to sensing feedback from the at least one muscle or the at least one joint activity sensor to cause a flexible compression garment to selectively compress against or selectively relieve compression against at least one body part of a subject. Such selective compression or relief of compression against the at least one body part can improve muscle functioning, joint functioning, or can be used for training or teaching an activity (e.g., a sport) or for rehabilitation.

In an embodiment, a garment system includes at least one flexible compression garment configured to be worn on at least one body part of a subject, one or more activity sensors supported by the at least one flexible compression garment, one or more actuators positioned relative to the at least one flexible compression garment and configured to cause the at least one flexible compression garment to selectively compress against or selectively relieve compression against the at least one body part, and a control system operably coupled to the one or more actuators and further operably coupled to the one or more activity sensors to receive the one or more sensing signals therefrom. The at least one flexible compression garment defines an interior space configured to receive the at least one body part. The one or more activity sensors are positioned and configured to sense at least one characteristic of at least one muscle or at least one joint of the at least one body part that is related to muscle activity or joint activity thereof, with the one or more activity sensors being further configured to output one or more sensing signals indicative of the at least one characteristic. The control system includes control electrical circuitry configured to direct the one or more actuators to cause the at least one flexible compression garment to selectively compress against or selectively relieve compression against the at least one body part responsive to the one or more sensing signals from the one or more activity sensors.

In an embodiment, a method of using a garment system is disclosed. At least one flexible compression garment of the at least one garment system is worn on at least one body part of a subject. The garment system includes one or more activity sensors configured to sense at least one characteristic of at least one muscle or at least one joint of the at least body part that is related to muscle activity or joint activity thereof and one or more actuators configured to cause the at least one flexible compression garment to selectively compress against or selectively relieve compression against the at least one body part. The at least one characteristic of the at least one muscle or the at least one joint of the at least one body part is sensed with the one or more activity sensors. Responsive to sensing the at least one characteristic via the one or more activity sensors, the one or more actuators are actuated to cause the at least one flexible compression garment to selectively compress against or selectively relieve compression against the at least one body part.

Features from any of the disclosed embodiments may be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
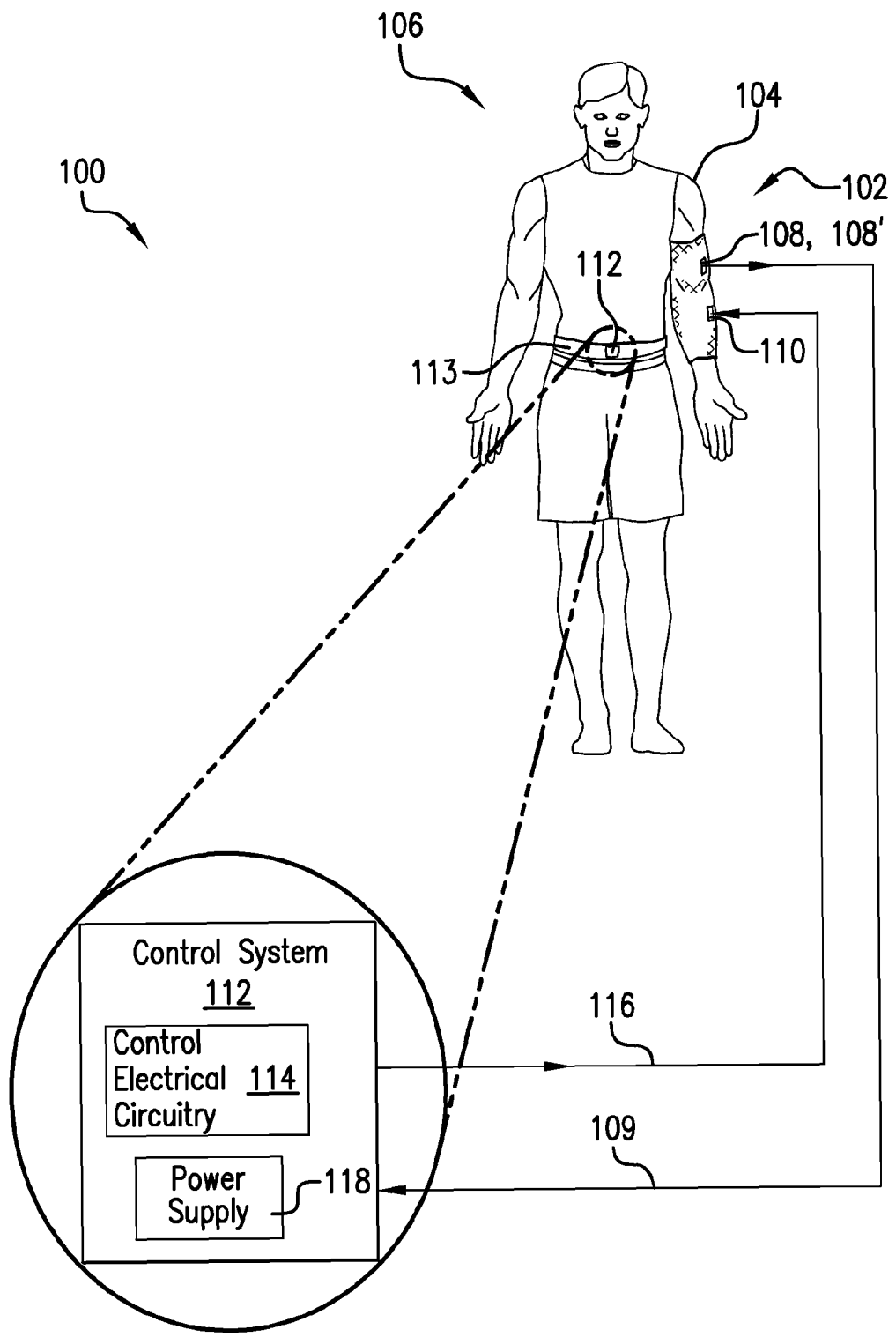
FIG. 1 is a diagrammatic view of a garment system according to an embodiment.

Embodiments disclosed herein relate to a garment system including at least one muscle or at least one joint activity sensor, and at least one actuator that operates responsive to sensing feedback from the at least one muscle or the at least one joint activity sensor to cause a flexible compression garment to selectively compress against or selectively relieve compression against at least one body part of a subject. Such garment systems can selectively provide or relieve compression against the at least one body part. Such selective compression or relief of compression against the at least one body part can improve muscle functioning or joint functioning, or can be used for training or teaching an activity (e.g., a sport) or for rehabilitation. Embodiments disclosed herein also relate to methods of using such garment systems.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 is an illustration of a garment system 100 according to an embodiment. The garment system 100 includes a flexible compression garment 102 that is configured to be worn on at least one body part 104 of a subject 106 during use. The flexible compression garment 102 can be substantially tubular and configured to generally conform to the at least one body part 104 when worn thereon.

The flexible compression garment 102 can be made from any suitable material. For example, the flexible compression garment 102 can be made from neoprene, nylon, synthetic rubber, or any other suitable synthetic or natural fabric or polymeric material.

In the illustrated embodiment, the at least one body part 104 is an arm of the user, which includes a portion of the subject's 106 upper arm, forearm, and elbow joint therebetween that is received by the flexible compression garment 102. However, as discussed in more detail below, the garment systems disclosed herein can be employed on many other types of body parts. For example, the at least one body part 104 of the subject 106 can include at least a portion of a thigh and/or at least a portion of a lower leg, or at least a portion of a neck. As another example, the flexible compression garment 102 can be configured as a shirt, and the at least one body part 104 includes at least the chest of the subject 106.

The garment system 100 includes one or more activity sensors 108 that can be mounted on, embedded in, or otherwise supported by the flexible compression garment 102. The one or more activity sensors 108 are positioned and configured relative to the at least one body part 104 to sense at least one characteristic of at least one muscle or at least one joint of the at least body part 104 that is related to muscle activity or joint activity thereof of the at least body part 104 of the subject 106. For example, each or some of the one or more activity sensors 108 can be positioned adjacent to or proximate to the at least one muscle or the at least one joint of which activity is desired to be monitored. During use, the one or more activity sensors 108 output one or more sensing signals 109 indicative of the at least one characteristic. It is noted that the at least one muscle or at least one joint of which activity is to be sensed can include a plurality of muscles or a plurality joints. For example, in the case where the flexible compression garment 102 receives at least a portion of an upper arm and at least a portion of a forearm of the subject 106, the at least one muscle of the at least one body part 104 can include a plurality of muscles in each of the upper arm and lower arm of the at least one body part 104 and the at least one joint of the at least one body part 104 can include the elbow joint.

The garment system 100 further includes one or more actuators 110. The one or more actuators 110 are positioned relative to the flexible compression garment 102 and configured to cause the flexible compression garment 102 to selectively compress against or selectively relieve compression against the at least one body part 104 responsive to the one or more sensing signals 109 output by the one or more activity sensors 108. For example, the one or more actuators 110 can be embedded in the flexible compression garment 102, mounted interiorly inside of the flexible compression garment 102 in an interior space thereof in which the at least one body part 104 is received, or mounted exteriorly on the flexible compression garment 102.

The garment system 100 further includes a control system 112 operably coupled to the one or more activity sensors 108 and the one or more actuators 110. For example, the control system 112 can be wireless operably coupled to the one or more activity sensors 108 and the one or more actuators 110 or operably coupled via a wired connection, such as electrical wires. For example, the control system 112 can be sized and configured to be conveniently worn or carried by the subject 106, such as via straps 113 shown on the subject 106 in FIG. 1.

In an embodiment, the control system 112 further includes control electrical circuitry 114 configured to direct the one or more actuators 110 via one or more actuation signals 116 to cause the flexible compression garment 102 to selectively compress against or selectively relieve compression against the at least one body part 104 responsive to receiving the one or more sensing signals 109 from the one or more activity sensors 108. In an embodiment, the control system 112 further includes a power supply 118 (e.g., a battery, microbattery, a thin film battery, a stretchable/flexible power supply, a fuel cell, an energy harvester, a kinetic energy harvester, a triboelectric nanogenerator, or other suitable power supply) that can power at least some of the components of the garment system 100, such as the control electrical circuitry 114, the one or more activity sensors 108, or the one or more actuators 110.

As will be discussed in more detail below, instructions that the control electrical circuitry 114 of the control system 112 employs for directing and controlling the operation of the one or more activity sensors 108 and the one or more actuators 110 can be pre-programmed in the control electrical circuitry 114, or programmed by the subject 106 or other person such as a medical professional like a doctor, a nurse, a physical therapist, a trainer, etc. For example, the programming of the control electrical circuitry 114 can be effected via at least one of software, firmware, programmable logical devices, or other technique for controlling the one or more activity sensors 108 and the one or more actuators 110 or other components of the garment system 100 in a selected manner.

During use in some operational situations, responsive to the one or more activity sensors 108 sensing the at least one characteristic of the at least one muscle or the at least one joint of the at least body part 104 that is related to muscle activity or joint activity thereof, the control electrical circuitry 114 directs the one or more actuators 110 to selectively compress against the at least one body part 104 to provide more support thereto or to improve muscle or joint functioning, such as increased blood flow or increased oxygenation to the at least one muscle or at least one joint of the at least one body part 104. For example, responsive to the one or more activity sensors 108 sensing the at least one characteristic of the at least one muscle or the at least one joint of the at least body part 104 that is related to muscle activity or joint activity thereof is over a threshold level, the control electrical circuitry 114 directs the one or more actuators 110 to selectively compress against the at least one body part 104. For example, the compression applied by the one or more actuators can be a gradient of compression along the at least one body part 104. In a more specific embodiment, the control electrical circuitry 114 can direct the one or more actuators 110 to cause the flexible compression garment 102 to selectively compress against at least one first portion of the at least one muscle of the at least one body part 104 with a first level of compression and selectively compress against at least one second portion of the at least one muscle or a second muscle of the at least one body part 104 with a second level of compression that is different than the first level of compression. As another example, the compression applied by the one or more actuators 110 can be one or more compression pulses applied to the at least one body part 104.

During use in other operational situations, responsive to the one or more activity sensors 108 sensing the at least one characteristic of the at least one muscle or the at least one joint of the at least body part 104 that is related to muscle activity or joint activity thereof, the control electrical circuitry 114 directs the one or more actuators 110 to selectively relieve compression against the at least one body part 104, such as during a portion of an athletic activity in which the at least one muscle or the at least one joint of subject is minimally exerted or stressed, respectively. For example, responsive to the one or more activity sensors 108 sensing the at least one characteristic of the at least one muscle or the at least one joint of the at least body part 104 that is related to muscle activity or joint activity thereof is below a threshold level, the control electrical circuitry 114 directs the one or more actuators 110 to selectively relieve compression against the at least one body part 104.

In an embodiment, the garment system 100 can also be operated according to a feedback loop. For example, the control electrical circuitry 114 can direct the one or more actuators 110 to selectively compress or selectively relieve compression against the at least one body part 104 a first selected amount, followed by selectively compress or selectively relieve compression against the at least one body part 104 a second selected amount that is different than the first amount.

Although only one flexible compression garment 102 is shown in FIG. 1, in other embodiments, a plurality of flexible compression garments 102 can be worn on different body parts of the subject 106. In such an embodiment, each of the plurality of flexible compression garments 102 includes its own one or more activity sensors and one or more actuators that can be individually operably coupled to the control system 112 and independently operate according to directions from the control system 112.

As mentioned above, the one or more activity sensors 108 can be configured to sense at least one characteristic of the at least one muscle or the at least one joint of the at least body part 104. For example, the at least one characteristic can be at least one physical characteristic, at least one chemical characteristic (e.g., biochemical or biological), or at least one physiological characteristic of the at least one muscle or the at least one joint of the at least body part 104. More specifically, for example, the at least one characteristic can include at least one of nerve activity of the at least one muscle of the at least one body part 104, temperature of the at least one muscle or the at least one joint of the at least one body part 104, oxygenation of the at least one muscle or the at least one joint of the at least one body part 104, acoustic emission from the at least one muscle or the at least one joint of the at least one body part 104, or other suitable characteristic that can be correlated to muscle or joint activity. In an embodiment, the one or more activity sensors 108 are configured to only sense the at least one characteristic of the at least one muscle of the at least one body part 104, while in other embodiments, the one or more activity sensors 108 are configured to only sense the at least one characteristic of the at least one joint of the at least one body part 104.

In order to sense the at least one characteristic of the at least one muscle or the at least one joint, various different activity sensors can be used. For example, in any of the embodiments disclosed herein, the one or more activity sensors 108 can include at least one of an electromyography sensor, a thermal sensor, a muscle oxygenation sensor, an acoustic sensor, a chemical sensor, a biochemical sensor, or a biosensor. The one or more activity sensors 108 can be disposed at least partially on an interior surface of the flexible compression garment 102 defining an interior space that receives the at least one body part 104, or at least partially embedded in the flexible compression garment 102.

In an embodiment, the one or more activity sensors 108 are configured to sense onset of or a threshold level of muscle activity of the at least one muscle of the at least one body part 104. In such an embodiment, the control electrical circuitry 114 is configured to direct the one or more actuators 110 to selectively compress against the at least one body part 104 responsive to the one or more activity sensors 108 sensing the onset of muscle activity but prior to the muscle activity occurring. One suitable activity sensor configured to sense nerve impulses of the at least one muscle indicative of the onset of the muscle activity includes one or more electromyography sensors, which can be attached, adhered, or embedded within the flexible compression garment 102 or attached directly to the subject 106. For example, responsive to sensing the onset of muscle activity via the one or more electromyography sensors, the control electrical circuitry 114 can direct the one or more actuators 110 to cause the flexible compression garment 102 to selectively compress the at least one muscle or the at least one joint of the at least one body part 104. Examples of suitable electromyography sensors that can be used to practice one or more embodiments disclosed herein are disclosed in U.S. Patent Application Publication Nos. 20060058694 and 20130041235, and in Kim, et al., Science 333, 838-843 (2011), the disclosure of each of which is incorporated herein, in its entirety, by this reference.

In an embodiment, the one or more activity sensors 108 can include one or more passive infrared thermal sensors.

For example, each passive infrared thermal sensor is positioned on or in the flexible compression garment 102 and configured to sense infrared radiation from the at least one muscle of the at least one body part 104. An increase in the infrared radiation can be indicative of or correlated with increased muscle temperature, which can be indicative of increased muscle activity. A decrease in the infrared radiation can be indicative of or correlated with decreased muscle temperature, which can be indicative of decreased muscle activity. For example, responsive to sensing an increase in or a threshold level of infrared radiation, the control electrical circuitry 114 may direct the one or more actuators 110 to cause the flexible compression garment 102 to selectively compress the at least one muscle or the at least one joint of the at least one body part 104. As another example, responsive to sensing a decrease in or less than a threshold level of infrared radiation, the control electrical circuitry 114 can direct the one or more actuators 110 to cause the flexible compression garment 102 to selectively relieve compression against the at least one muscle or the at least one joint of the at least one body part 104 due to muscle activity decreasing.

When the one or more activity sensors 108 are configured to sense temperature of the at least one muscle directly or indirectly, in an embodiment, the flexible compression garment 102 can include one or more fluid channels through which coolant can flow, a fluid coolant reservoir, and a pump configured to pump the fluid coolant from the reservoir through the one or more fluid channels. Thus, in such an embodiment, the control electrical circuitry 116 can direct the pump to pump fluid coolant from the fluid coolant reservoir through the one or more fluid channels to help cool the at least one muscle.

In an embodiment, the one more activity sensors 108 can include one or more muscle oxygenation sensors. For example, each muscle oxygenation sensor can include a near infrared sensor positioned and configured to deliver light in the near infrared spectrum to the at least one muscle of the at least one body part 104 and detect light reflected from the at least one muscle (e.g., tissue), thereby sensing absorption of the near infrared light by the muscle that differs in oxygenated and deoxygenated tissues. Examples of near infrared sensors for measuring the oxygenation of muscle tissues that can be used to practice one or more embodiments disclosed herein are disclosed in Hamaoka, et al., Phil. Trans. R. Soc. A (2011) 369, 4591-4604, which is incorporated herein, in its entirety, by reference. Changes in the absorption of near infrared light from the at least one muscle can be correlated with or can be indicative of increased muscle oxygenation. For example, changes in the absorption of the near infrared light can be associated with increased exertion or decreased muscle oxygenation (e.g., associated with overwork, cramping, or claudication).

In an embodiment, responsive to sensing a change in muscle oxygenation, the control electrical circuitry 114 can direct the one or more actuators 110 to cause the flexible compression garment 102 to selectively compress or selectively relieve compression against the at least one muscle or at least one joint of the at least one body part 104. For example, responsive to sensing an increase in muscle oxygenation over a threshold level, the control electrical circuitry 114 can direct the one or more actuators 110 to cause the flexible compression garment 102 to selectively compress the at least one muscle or at least one joint of the at least one body part 104. For example, responsive to sensing a decrease in muscle oxygenation below a threshold level, the control electrical circuitry 114 can direct the one or more actuators 110 to cause the flexible compression garment 102 to selectively relieve compression against the at least one muscle or the at least one joint of the at least one body part 104 due to muscle activity decreasing. In other embodiments, the one or more oxygenation sensors can be used to sense a change in joint oxygenation.

In an embodiment, the one or more activity sensors 108 can include multiple near infrared source-detector pairs that can measure spatial and regional differences in skeletal muscle oxygenation and/or localized changes of the at least one body part 104. For example, responsive to sensing a localized decrease in infrared radiation below a threshold level indicative of significantly decreased muscle oxygenation and blood flow associated with a muscle cramp, the control electrical circuitry 114 can direct the one or more actuators 110 to cause the flexible compression garment 102 to selectively compress against the at least one muscle of the at least one body part 104 to provide localized support and increase blood pressure. For example, responsive to sensing a varied decrease in infrared radiation indicative of a gradient of decreased muscle oxygenation and blood flow associated with muscle overexertion, the control electrical circuitry 114 can direct the one or more actuators 110 to cause the flexible compression garment 102 to selectively compress against at least one first portion of the at least one muscle of the at least one body part 104 with a first level of compression and selectively compress against at least one second portion of the at least one muscle or a second muscle of the at least one body part 104 with a second level of compression or to cause the flexible compression garment 102 to intermittently selectively compress against a part of the at least one muscle of the at least one body part 104 to provide localized to increase blood flow to the muscle.

In an embodiment, the one more activity sensors 108 can include one or more acoustic transducers configured to irradiate the at least one muscle or the at least one joint of the at least one body part 104 with acoustic radiation and receive reflected acoustic radiation responsive thereto. The received reflected acoustic radiation can be correlated with or can be indicative of muscle activity or joint activity of the at least one muscle or the at least one joint of the at least one body part 104. For example, a relatively stronger/more intense reflected acoustic radiation received by the one or more acoustic transducers can be indicative of relatively tenser, more active muscles, while a relatively weaker/less intense reflected acoustic radiation received by the one or more acoustic transducers can be indicative of relatively looser, less active muscles.

In an embodiment, the acoustic transducer includes an ultrasound transducer, and each of the acoustic radiation and the reflected acoustic radiation includes ultrasound radiation. The received reflected ultrasound radiation can be correlated with or can be indicative of at least one characteristic of a muscle activity or a joint activity of the at least one body part 104. For example, altered echogenicity detected by the one or more acoustic transducers can be indicative of swelling or inflammation of the at least one muscle. For example, altered echogenicity detected by the one or more acoustic transducers can be indicative of joint effusion of the at least one joint. For example, Doppler ultrasound sensing of the at least one muscle can detect increased blood flow within the at least one muscle, indicating increased activity of the at least one muscle. For example, Doppler ultrasound sensing of a ligament or tendon may detect limited activity within the ligament or tendon, indicating stress to the region. In an embodiment, responsive to the one or more acoustic transducers detecting a change in at least one characteristic of the at least one muscle or the at least one joint of the at least one body part 104, the control electrical circuitry 114 can direct the one or more actuators 110 to cause the flexible compression garment 102 to selectively compress or selectively relieve compression against the at least one muscle or at least one joint. For example, responsive to sensing echogenicity indicating an increase in muscle or joint activity, the control electrical circuitry 114 can direct the one or more actuators 110 to cause the flexible compression garment 102 to selectively compress the at least one muscle or at least one joint of the at least one body part 104. For example, responsive to sensing echogenicity indicating a decrease in muscle or joint activity, the control electrical circuitry 114 can direct the one or more actuators 110 to cause the flexible compression garment 102 to selectively relieve compression against the at least one muscle or at least one joint of the at least one body part 104 due to muscle activity decreasing. For example, responsive to sensing echogenicity indicating inflammation in the least one muscle or the at least one joint, the control electrical circuitry 114 can direct the one or more actuators 110 to cause the flexible compression garment 102 to selectively compress, and thereby support, the at least one muscle or at least one joint of the at least one body part 104.

In an embodiment, the one more activity sensors 108 can include one or more acoustic myography sensors positioned and configured to sense acoustic emission from the at least one muscle of the at least one body part 104. An example of an acoustic myography sensor for sensing muscle use suitable for practicing one or more embodiments disclosed herein is disclosed in Harrison, et al., Physiol Rep, 1(2): e00029; 2013, the disclosure of which is incorporated herein, in its entirety, by this reference. For example, responsive to sensing a high frequency by the acoustic myography sensor, indicative of increased muscle use, the control electrical circuitry 114 may direct the one or more actuators 110 to cause the flexible compression garment 102 to selectively compress the at least one muscle of the at least one body part 104.

In an embodiment, the one more activity sensors 108 can include one or more acoustic sensors positioned and configured to sense acoustic emission from the at least one joint of the at least one body part 104. For example, the one or more acoustic sensors can be positioned adjacent to or proximate to the at least one joint (e.g., an elbow as illustrated in FIG. 1, wrist, or knee) so that the one or more acoustic sensors can receive acoustic emission from the at least one joint that can be indicative of joint problems, such as aggravation of an arthritic or an osteoarthritic condition and resultant arthralgia. For example, responsive to sensing acoustic emission or an increase in acoustic emission from the at least one joint, the control electrical circuitry 114 may direct the one or more actuators 110 to cause the flexible compression garment 102 to selectively compress the at least one joint and the at least one muscle around the at least one joint of the at least one body part 104 to thereby alleviate arthralgia.

In an embodiment, the one more activity sensors 108 can include one or more of at least one chemical sensor, at least one biochemical sensor, or at least one biosensor configured to detect an analyte from the at least one muscle or the at least one joint of the at least one body part 104. For example, at least one chemical sensor, at least one biochemical sensor, or at least one biosensor can be configured to detect at least one of an ion, a salt, glucose, a lactate, lactic acid, or an inflammatory molecule from the at least one muscle or the at least one joint. For example, responsive to sensing an increase in lactic acid in the at least one muscle by a biosensor indicative of muscle fatigue, the control electrical circuitry 114 can direct the one or more actuators 110 to cause the flexible compression garment 102 to selectively compress the at least one muscle of the at least one body part 104.

In an embodiment, one more optional additional types of activity sensors 108' can be incorporated into the flexible compression garment 102 and operably coupled to the control electrical circuitry 114. For example, the one or more additional types of activity sensors can include one or more low profile heart rate sensors that are configured to sense a heart rate of the subject 106. In an embodiment, the one or more heart rate sensors can include an electrocardiography sensor or a pulse sensor (e.g., a pulse oximetry sensor). In an embodiment, the one or more heart rate sensors can include a pulse sensor for measuring a peripheral pulse, such as in a limb. Thus, in an embodiment, the pulse sensor can be selectively positioned on the flexible compression garment 102 to be proximate to an artery, such as a relatively large artery on the at least one body part 104 of the subject 106. Examples of low profile, stretchable and flexible heart rate and electrocardiography sensors are described in U.S. Patent Application Publication Nos. 20060058694 and 20130041235, previously incorporated by reference.

Responsive to sensing an increase in the heart rate of the subject 106 indicative of increased muscle activity, the control electrical circuitry 114 can direct the one or more actuators 110 to cause the flexible compression garment 102 to selectively compress the at least one muscle or at least one joint of the at least one body part 104. As another example, responsive to sensing a decrease in the heart rate of the subject 106 indicative of decreased muscle activity, the control electrical circuitry 114 can direct the one or more actuators 110 to cause the flexible compression garment 102 to selectively relieve compression against the at least one muscle or at least one joint of the at least one body part 104 due to muscle activity decreasing.

By way of another example and having applicability to any of the activity sensors 108 or optional additional types of activity sensors 108' disclosed herein, in an embodiment, actuating the one or more actuators 110 to cause the flexible compression garment 102 to selectively compress against the at least one body part 104 is responsive to the at least one characteristic sensed by one or more activity sensors being indicative of the at least one muscle being injured or being strained past a strain limit. In another embodiment having applicability to any of the activity sensors 108 disclosed herein, actuating the one or more actuators 110 to cause the flexible compression garment 102 to selectively compress against or selectively relieve compression against the at least one body part 104 is responsive to the at least one characteristic sensed by one or more activity sensors 108 being indicative of the at least one muscle being exerted. In another embodiment having applicability to any of the one or more activity sensors 108 disclosed herein, actuating the one or more actuators 110 to cause the flexible compression garment 102 to selectively compress against or selectively relieve compression against the at least one body part 104 can be responsive to the at least one characteristic sensed by the one or more activity sensors 108 being indicative of the at least one muscle being not exerted beyond a threshold. For example, the one or more activity sensors 108 can indicate that the at least one muscle is not being exerted at or near a physiological or functional limit thereof, and the flexible compression garment 102 adjusts the amount of compression applied to the at least one muscle to cause the muscle work harder, such as during strength training.

The one or more actuators 110 can be selected from a number of suitable different types of actuators. Additionally, as will be discussed in more detail below, the one or more actuators 110 may be positioned in a number of different configurations. For example, in any of the embodiments disclosed herein, the one or more actuators 110 can include at least one of one or more electroactive polymer actuators, one or more electroactive metallic actuators, one or more motors, or one or more hydraulic actuators.

In an embodiment, the one or more electroactive polymer actuators include one or more actuator elements at least partially formed from ferroelectric polymers, dielectric elastomers, or electrostrictive graft elastomers. Responsive to a voltage applied by the power supply 118 based on instructions from the control electrical circuitry 114, the electroactive polymer actuators may increase or decrease in length, diameter, or other dimension depending on the polarity of the applied voltage to cause the flexible compression garment 102 to selectively compress or relieve compression of the at least one body part 104. For example, suitable electroactive polymers for the electroactive polymer actuators include at least one of NuSil CF19-2186 commercially available from NuSil Technology of Carpinteria, Calif., silicone elastomers, acrylic elastomers (e.g., VHB 4910 acrylic elastomer commercially available from 3M Corporation of St. Paul, Minn.), polyurethanes, thermoplastic elastomers, copolymers comprising polyvinylidene difluoride ("PVDF"), pressure-sensitive adhesives, fluoroelastomers, polymers comprising silicone and acrylic moieties, or other suitable electroactive polymers.

In an embodiment, the one or more electroactive metallic actuators include one or more actuator elements at least partially formed from a shape memory material. For example, the shape memory material can include a nickel-titanium shape memory alloy, such as nitinol or other suitable nickel-titanium alloy composition. Responsive to the power supply 118 passing a current through the shape memory material to heat the shape memory material based on instructions from the control electrical circuitry 114, the electroactive metallic actuators may increase or decrease in length, diameter, or other dimension depending on the temperature to which the shape memory material is heated to cause the flexible compression garment 102 to selectively compress or relieve compression of the at least one body part 104.

Examples of such nickel-titanium shape memory alloys are currently commercially available from Dynalloy, Inc. and sold under the trade name Flexinol®. Flexinol HT® has a transition temperature of about 194° F., with an activation start temperature at about 190° F. and an activation finish temperature at about 208° F. Such nickel-titanium alloys can gradually and controllably contract in length about 2% to about 5% of their length or other dimension as they are heated from the activation start temperature to the activation finish temperature.

In an embodiment, the one or more motors include one or more micro-electro-mechanical actuators. For example, the one or more micro-electro-mechanical motors can include one or more micro-piezoelectric actuators, one or more micro-electrostatic actuators, or one or more micro-electromagnetic actuators. Examples of suitable micro-electromechanical motors that can be used to practice one or more embodiments disclosed herein are disclosed in Acoust. Sci. & Tech. 31, 2 (2010), the disclosure of which is incorporated herein, in its entirety, by this reference. As another example, one suitable micro-piezoelectric actuator is New Scale's SQUIGGLE™ motor.

Figure 2A:
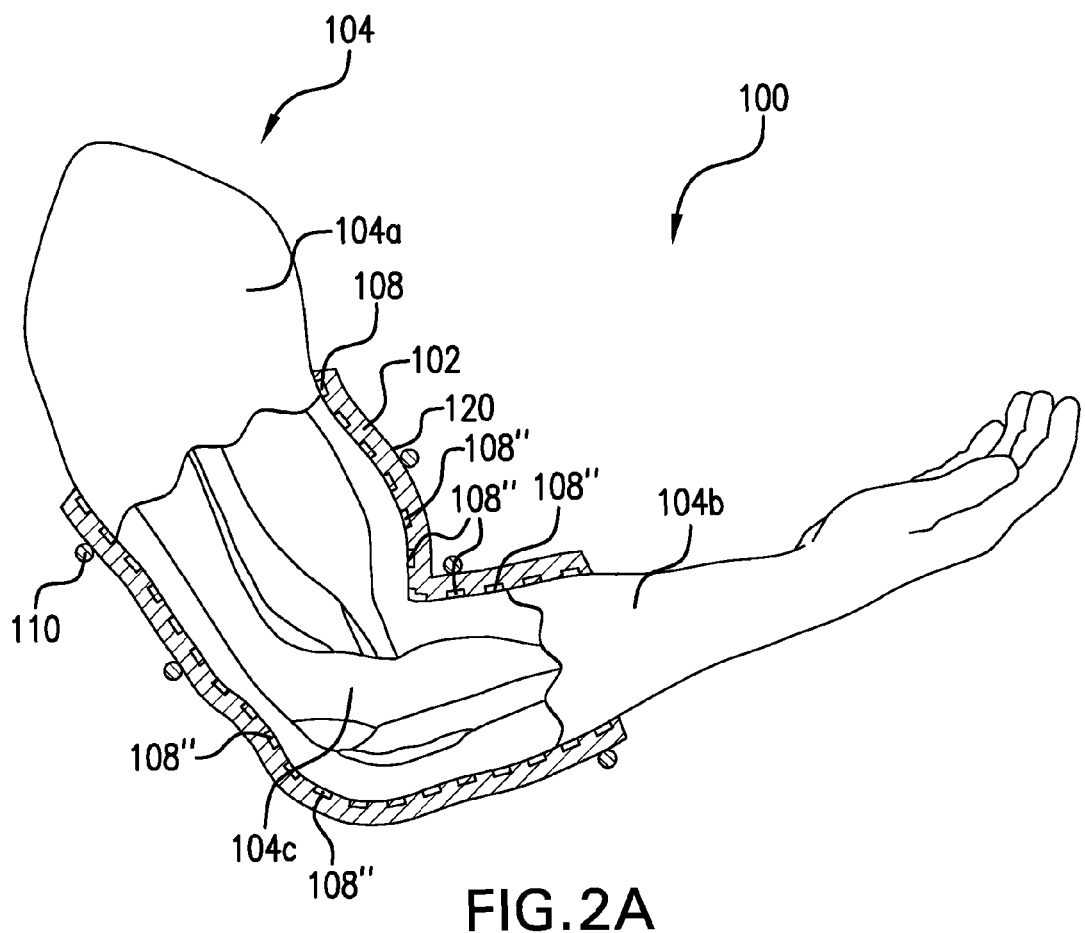
FIG. 2A is an isometric cutaway view of a flexible compression garment worn on an arm of a subject of the garment system shown in FIG. 1 according to an embodiment.
Figure 2B:
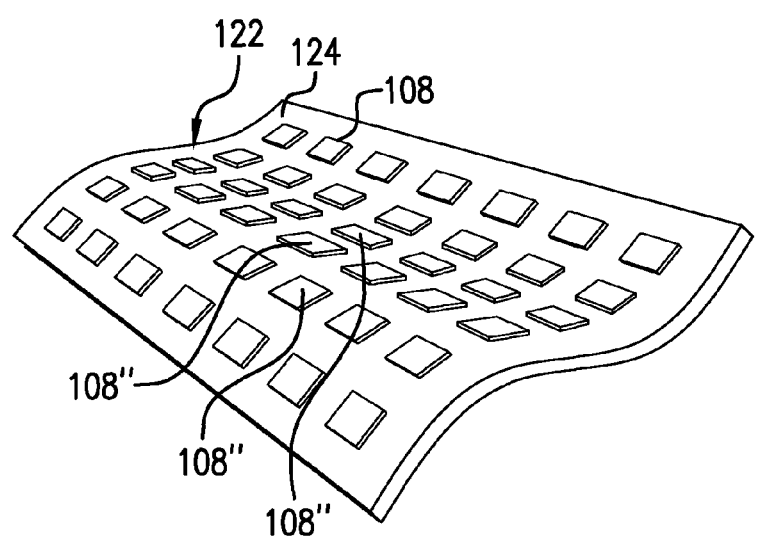
FIG. 2B is an isometric cutaway view of a section of the flexible compression garment shown in FIG. 2A, without the flexible compression garment shown being worn an arm of a subject.

FIGS. 2A and 2B are an isometric cutaway views of an embodiment of the flexible compression garment 102 of the garment system shown in FIG. 1, which is worn on the at least one body part 104 of the subject 106, according to an embodiment. In the illustrated embodiment shown in FIGS. 2A and 2B, the at least one body part 104 is an arm of the subject, which includes an upper arm 104a, a forearm 104b, and an elbow joint 104c connecting the upper arm 104a and the forearm 104b together. The flexible compression garment 102 defines an exterior 120, and the one or more actuators 110 are configured as a single coiled actuator extending about a portion of the exterior 120 of the flexible compression garment 102. For example, the single coiled actuator can extend circumferentially along the exterior 120 of the flexible compression garment 102 in a substantially helical path and is positioned and configured to increase or decrease an interior space 122 (FIG. 2B) defined by an interior surface 124 (FIG. 2B) of the flexible compression garment 102 responsive to actuation thereof. However, in other embodiments, the one or more actuators 110 such as the single coiled actuator can be embedded internally within the flexible compression garment 102.

Referring to FIG. 2B, in the illustrated embodiment, the activity sensors 108 may be positioned on or at least partially embedded within the interior surface 124 of the flexible compression garment 102. For example, when at least some of the activity sensors 108 are configured as acoustic sensors for sensing acoustic emission from the elbow joint 104c, such activity sensors 108 can be positioned on or in the interior surface 124 of the flexible compression garment 102 so that they are located at or near the elbow joint 104c (or other joint, such as one that can be affected by arthritis) and labeled as activity sensors 108" in FIGS. 2A and 2B as merely an example.

Figure 2C:
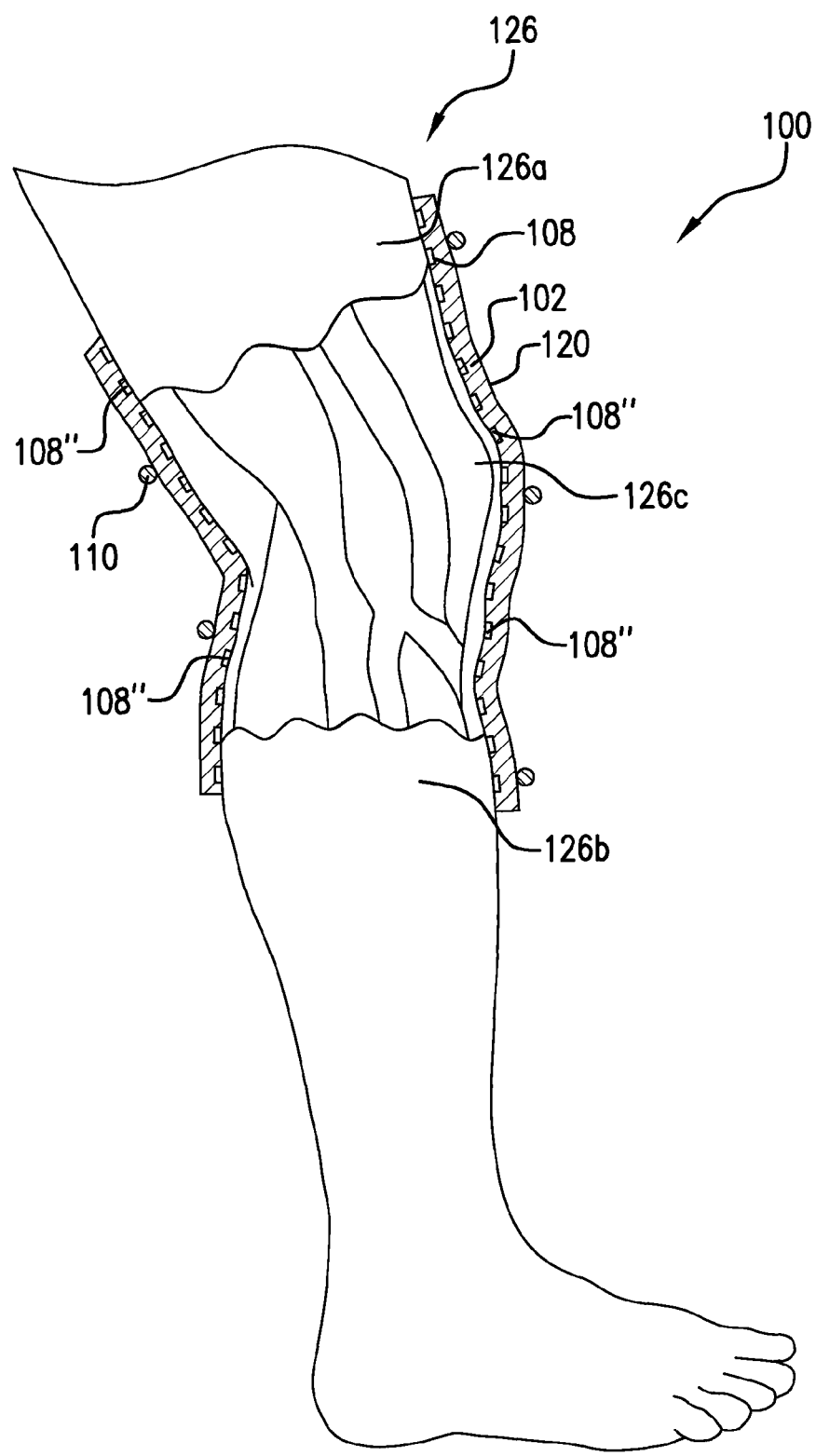
FIG. 2C is an isometric cutaway view of an embodiment of a flexible compression garment worn on a leg of a subject.
Figure 2D:
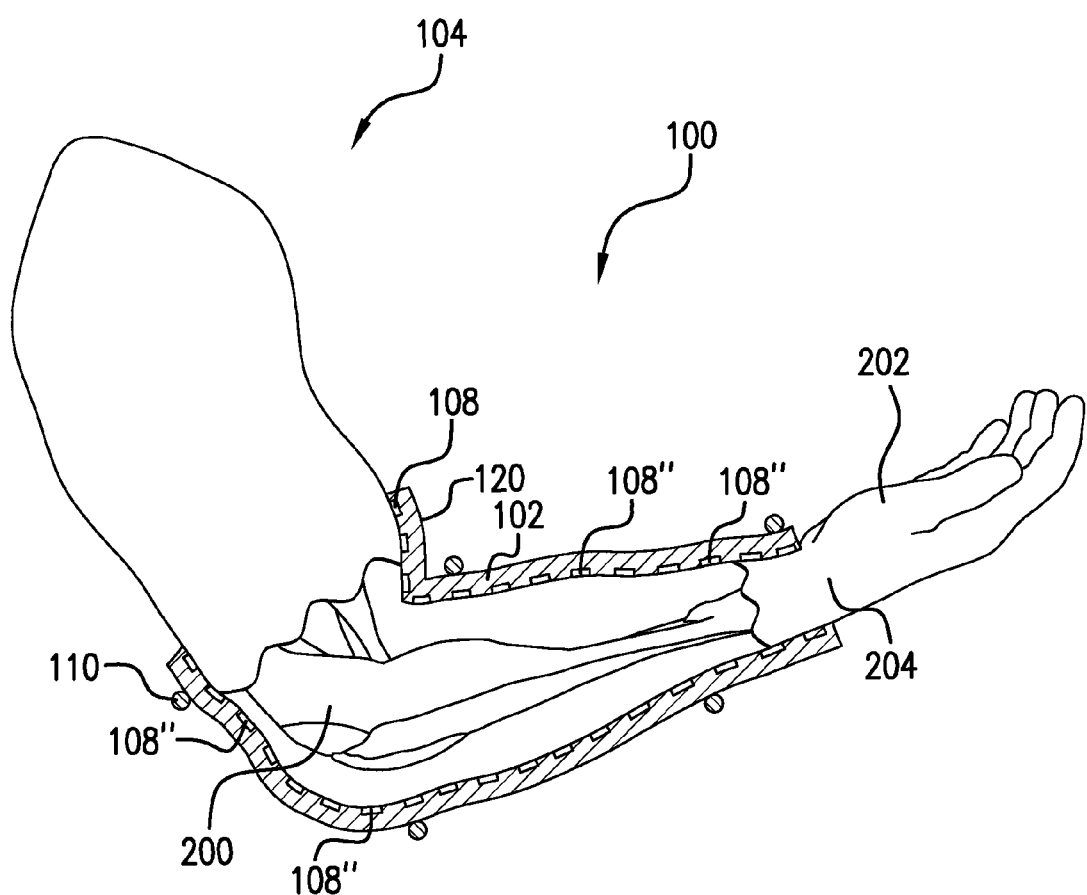
FIG. 2D is an isometric cutaway view of an embodiment of a flexible compression garment worn on a forearm and hand of a subject.

As previously discussed, the garment systems disclosed herein can be used on a number of different body parts besides an arm. For example, the at least one body part 104 can include a portion of a thigh, a portion of a lower leg, a portion of a hand, a portion of a foot, or a portion of a neck. FIG. 2C is an isometric cutaway view of an embodiment of the flexible compression garment 102 worn on a leg 126 of the subject 106. The flexible compression garment 102 can be configured to extend around a thigh 126a, a lower leg 126b, and a knee 126c that connects the thigh 126a and lower leg 126b together. As another example, FIG. 2D is an isometric cutaway view of an embodiment of the flexible compression garment 102 configured to be worn on a forearm 200, hand 202, and wrist 204 of the subject 106. Of course, in other embodiments, the flexible compression garment 102 can be configured for other body parts, such as the upper arm and shoulder, or neck of the subject 106. In other embodiments, the flexible compression garment 102 can be configured for other body parts that do not include a joint, such as a portion of a limb including, but not limited to, all or part of a thigh, a calf, a forearm, or an upper arm of the subject 106.

Figure 3A:
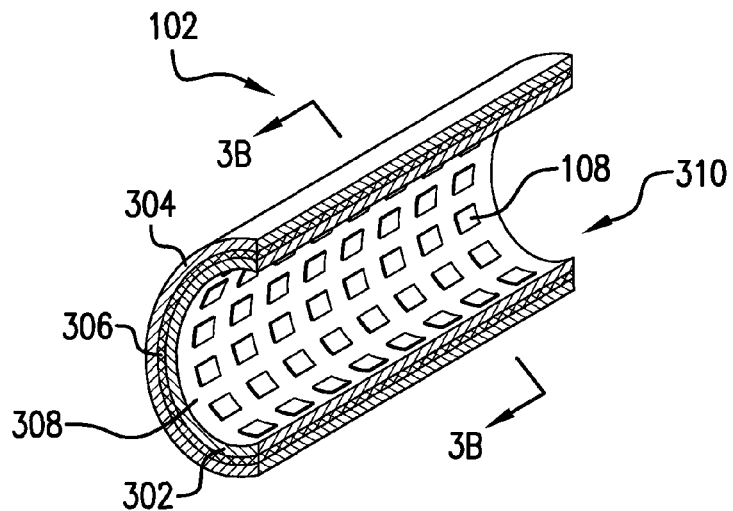
FIG. 3A is an isometric cutaway view of the flexible compression garment shown in FIG. 1 according to an embodiment.
Figure 3B:
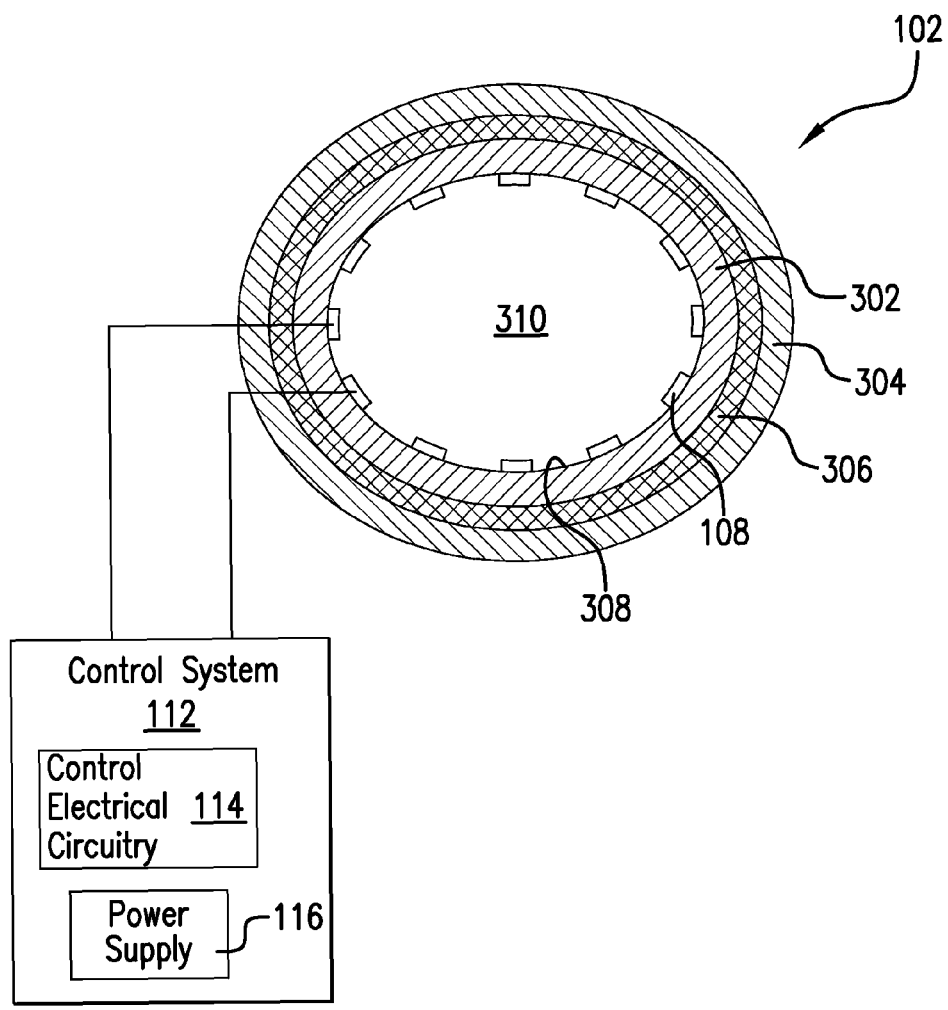
FIG. 3B is a cross-sectional view of the flexible compression garment shown in FIG. 3A taken along line 3B-3B thereof.

FIGS. 3A and 3B are isometric cutaway and cross-sectional views of the flexible compression garment 102 shown in FIG. 1 according to an embodiment. In the illustrated embodiment, the flexible compression garment 102 includes an inner garment body 302, an outer garment body 304, and a substantially tubular actuator 306 disposed between the inner garment body 302 and the outer garment body 304 in a concentric arrangement. For example, the substantially tubular actuator 306 is illustrated as being embedded within the flexible compression garment 102 and held between the inner garment body 302 and the outer garment body 304. As merely an example, the substantially tubular actuator 306 can be made from an electroactive polymer or a tube of shape memory alloy that is responsive to an appropriate actuation stimulus from the power supply 116 of the control system 112 so that a volume of an inner space 310 defined by the inner garment body 302 can increase or decrease responsive to actuation of the substantially tubular actuator 306.

In the illustrated embodiment, the one or more activity sensors 108 are disposed on an interior surface 308 of the inner garment body 302 that defines the interior space 310. However, in other embodiments, the one or more activity sensors 108 may be at least partially embedded within the inner garment body 302.

During use in some operational situations, responsive to the one or more activity sensors 108 sensing the at least one characteristic of the at least one muscle or the at least one joint of the at least body part 104 that is related to muscle activity or joint activity thereof, the control electrical circuitry 114 of the control system 112 directs the substantially tubular actuator 306 to selectively compress against the at least one body part 104 to provide more support thereto or to improve muscle or joint functioning. During use in other operational situations, responsive to the one or more activity sensors 108 sensing the at least one characteristic of the at least one muscle or the at least one joint of the at least body part 104 that is related to muscle activity or joint activity thereof, the control electrical circuitry 114 of the control system 112 directs the substantially tubular actuator 306 to selectively relieve compression against the at least one body part 104, such as during a portion of an athletic activity in which the at least one muscle or the at least one joint of subject is minimally exerted or stressed, respectively. During use in other operational situations, responsive to the one or more activity sensors 108 sensing the at least one characteristic of the at least one muscle or the at least one joint of the at least body part 104 that is related to muscle activity or joint activity thereof, the control electrical circuitry 114 of the control system 112 directs the substantially tubular actuator 306 to selectively compress against the at least one body part 104 or to selectively relieve compression against the at least one body part 104, such as to aid a particular action of the at least one muscle or the at least one joint. For example, the particular action can be an athletic action undertaken by at least one particular limb, such as an arm swinging a bat or club.

Figure 3C:
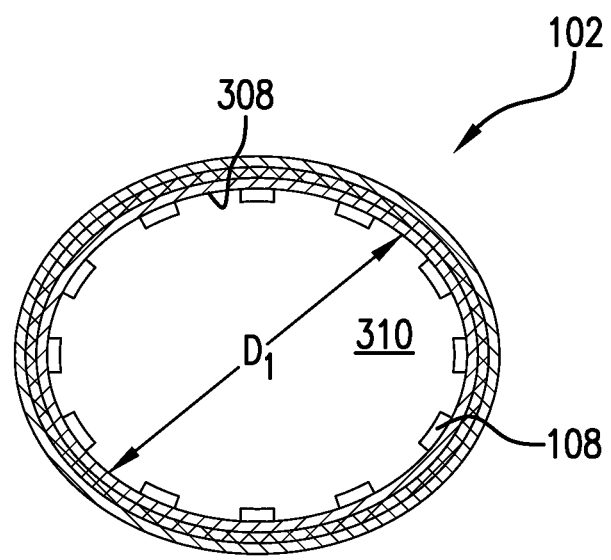
FIG. 3C is a cross-sectional view of the flexible compression garment shown in FIG. 3A prior to actuation of one or more actuators or at a low actuation level.
Figure 3D:
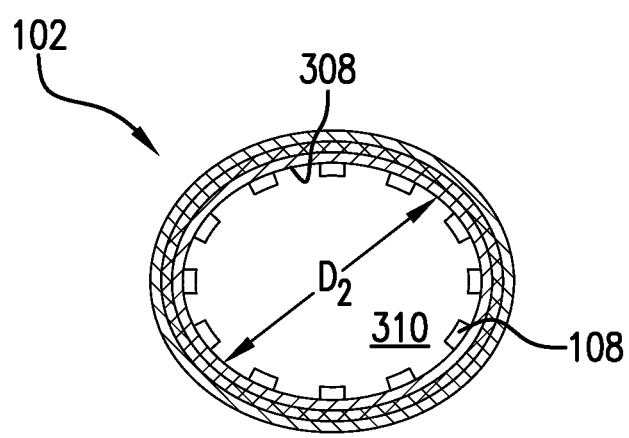
FIG. 3D is a cross-sectional view of the flexible compression garment shown in FIG. 3A after actuation of one or more actuators or at a relatively higher actuation level than in FIG. 3C.

FIGS. 3C and 3D are cross-sectional views of the flexible compression garment 102 shown in FIG. 3A prior to actuation of the actuator 306 or at a low actuation level, and after actuation of the actuator 306 or at a relatively higher actuation level than in FIG. 3C, respectively. As shown in FIG. 3C, prior actuation of the actuator 306 or at a low actuation level, the interior space 310 of the flexible compression garment 102 exhibits a relatively larger diameter D1 or other lateral dimension. As shown in FIG. 3D, after actuation of the actuator 306 or at a relatively higher actuation level than in FIG. 3C, the actuator 306 selectively compresses the flexible compression garment 102 against at least one body part of the subject such that the interior space 310 of the flexible compression garment 102 exhibits a relatively smaller diameter D2 or other lateral dimension. This contraction of the flexible compression garment 102 can be used to apply selective amounts of compression forces to the at least one body part of the subject. For example, the actuator 306 can cause narrowing of substantially the entire flexible compression garment 102 to the smaller diameter D2.

Figure 4:
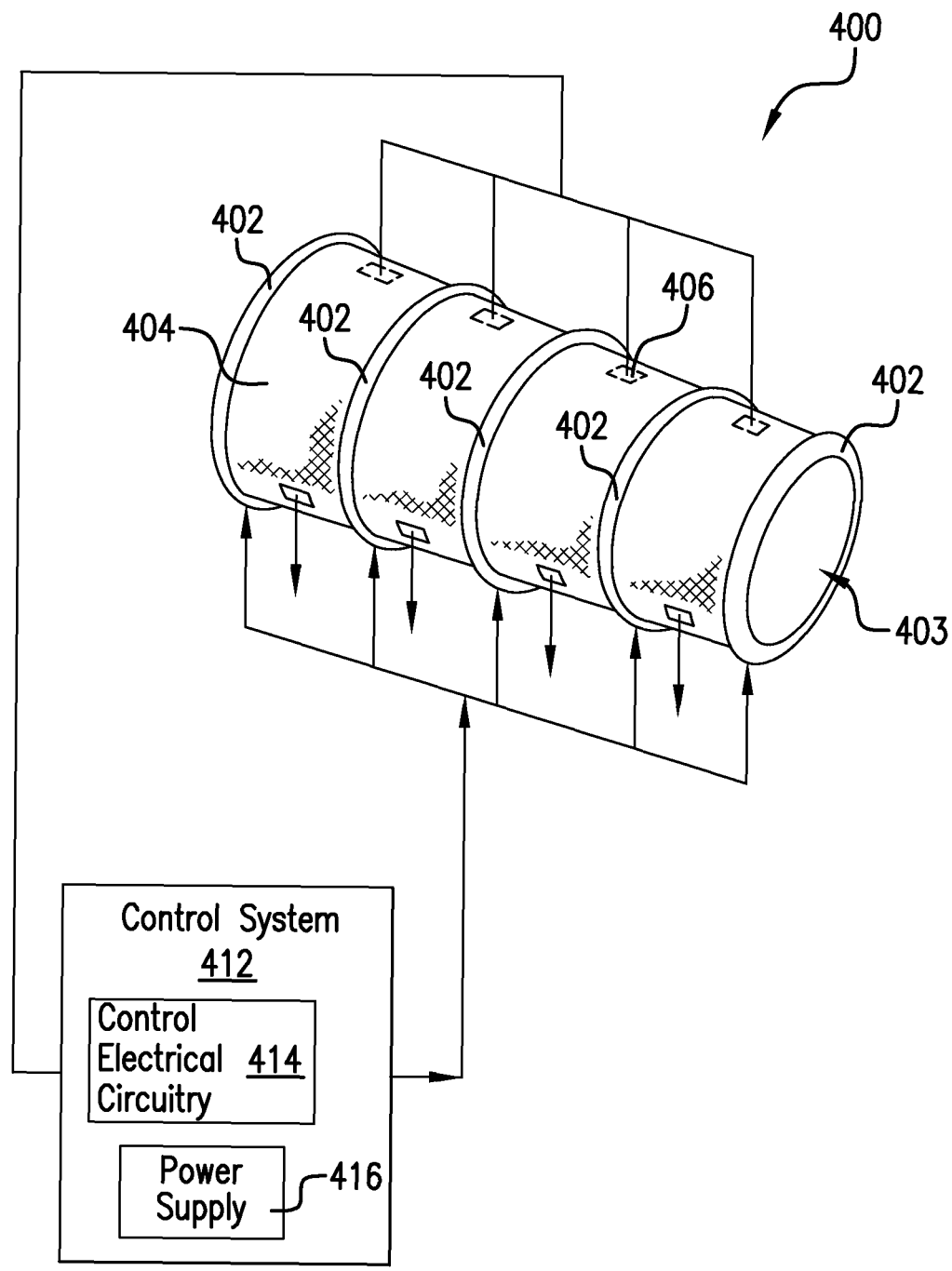
FIG. 4 is an isometric view of an embodiment of a garment system including a plurality of ring-shaped actuators.

FIG. 4 is an isometric view of an embodiment of a garment system 400 including a plurality of ring-shaped actuators 402. The garment system 400 includes a flexible compression garment 404 that can be made from the same materials as the flexible compression garment 102. The flexible compression garment 404 defines an interior space 403 for receiving at least one body part of a subject, such as an arm, leg, or other body part.

The plurality of ring-shaped actuators 402 are longitudinally spaced from each other. In the illustrated embodiment, the plurality of ring-shaped actuators 402 are disposed circumferentially about an exterior of the flexible compression garment 404. However, in other embodiments, the plurality of ring-shaped actuators 402 can be at least partially embedded within the flexible compression garment 404. As merely an example, each of the plurality of ring-shaped actuators 402 can be made from a ring electroactive polymer or a ring of shape memory alloy that is responsive to an appropriate actuation stimulus from a power supply 416 of a control system 412.

The garment system 400 further includes one or more activity sensors 406, which can be configured as any of the activity sensors disclosed herein. In the illustrated embodiment, the one or more activity sensors 406 are disposed within the interior space 403 of the flexible compression garment 402. However, in other embodiments, the one or more activity sensors 408 can be embedded within the flexible compression garment 402.

The control system 412 functions the same or similarly to the control system 112 in FIG. 1. For example, the control system 412 is operably coupled to the one or more activity sensors 408 and the plurality of ring-shaped actuators 402. Thus, during use in some operational situations, responsive to the one or more activity sensors 408 sensing the at least one characteristic of the at least one muscle or the at least one joint of the at least body part that is related to muscle activity or joint activity thereof, the control electrical circuitry 414 of the control system 412 directs the plurality of ring-shaped actuators 402 to selectively compress against the at least one body part to provide more support thereto or to improve muscle or joint functioning. Thus, the actuation of each of the plurality of ring-shaped actuators 402 decreases a diameter thereof. During use in other operational situations, responsive to the one or more activity sensors 408 sensing the at least one characteristic of the at least one muscle or the at least one joint of the at least body part that is related to muscle activity or joint activity thereof, the control electrical circuitry 414 of the control system 412 directs the plurality of ring-shaped actuators 402 to selectively relieve compression against the at least one body part, such as during a portion of an athletic activity in which the at least one muscle or at least one joint of a subject is minimally exerted or stressed, respectively. Thus, the actuation of each of the plurality of ring-shaped actuators 402 increases a diameter thereof.

Figure 5:
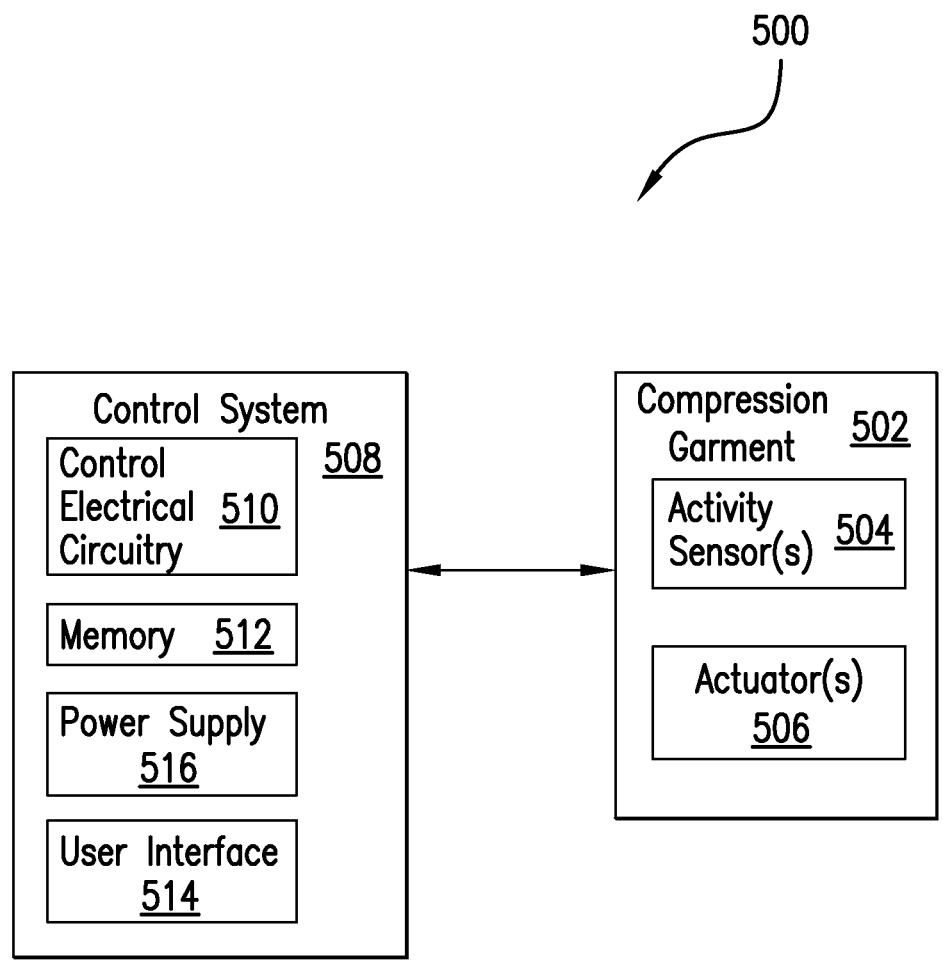
FIG. 5 is a functional block diagram of an embodiment of a garment system.

In some embodiments, the garment systems disclosed herein can include memory and a user interface that enables the subject or another person to program the manner in which the garment system operates. For example, FIG. 5 is a functional block diagram of an embodiment of a garment system 500. The garment system 500 includes a compression garment 502 including one or more activity sensors 504 and one or more actuators 506, as described in any of the embodiments disclosed herein. The garment system 500 further includes a control system 508 operably coupled to the one or more activity sensors 504 and the one or more actuators 506. The control system 508 includes control electrical circuitry 510 that controls the operation of the one or more activity sensors 504 or the one or more actuators 506, memory 512 operably coupled to the control electrical circuitry 510 that can be programmed with instructions via a user interface 514, and a power supply 516 that powers some or all of the components of the garment system 500.

The memory 512 can be programmed via the user interface 514 so that instructions for the operation of the garment system 500 are stored thereon. For example, the user interface 514 can include a keypad, monitor, touch screen, voice command recognition, desktop computer, laptop computer, cell phone, or combinations thereof that is operably coupled to the control electrical circuitry 510 of the control system 508. The user interface 504 can be operably coupled to the control electrical circuitry 510 via a wireless or wired communication connection. The subject that wears the garment system 500 or another party (e.g., a medical professional) can program instructions into the memory 512 for the operation of the one or more activity sensors 504 and the one or more actuators 506 via the user interface 514. Any method of operation for any of the garment systems disclosed herein can be programmed into the memory 512 with suitable instructions, as needed or desired. In an embodiment, the memory 512 is configured to store sensing data corresponding to the one or more sensing signals from the one or more activity sensors 504 and actuation data corresponding to the selective compression or the selective relief of compression of the flexible compression garment 502. Such sensing data and actuation data can be downloaded by the subject or other person (e.g., a medical professional) for analysis.

During operation, the control circuitry 510 accesses and receives instructions from the memory 512 and directs the sensing operations of the one or more activity sensors 504 and actuation of the one or more actuators 506 at least partially based on instructions stored in the memory 512. For example, responsive to the instructions stored in the memory 512, the control system 508 can direct the one or more actuators 504 to cause the compression garment 502 to selectively compress against at least one part of the subject wearing the compression garment 502 responsive to the one or more activity sensors 504 sensing increased or sufficient muscle or joint activity of the subject. As another example, responsive to the instructions stored in the memory 512, the control system 508 can direct the one or more actuators 504 to cause the compression garment 502 to selectively relieve compression against the at least one part of the subject wearing the compression garment 502 responsive to the one or more activity sensors 504 sensing decreased or relatively low muscle or joint activity of the subject.

In an embodiment, the memory 512 stores sensing data corresponding to the one or more sensing signals from the one or more activity sensors 504 and stores actuation data corresponding to the selective compression or the selective relief of compression of the flexible compression garment 502, which can be downloaded by any of the user interfaces 514 disclosed herein (e.g., a cell phone, desktop computer, or laptop computer) or other computing device. For example, the user interface 514 can download the sensing data and the actuation data such as frequency and duration of compression and decompression of the at least one least body part via the flexible compression garment 502.

Figure 6:
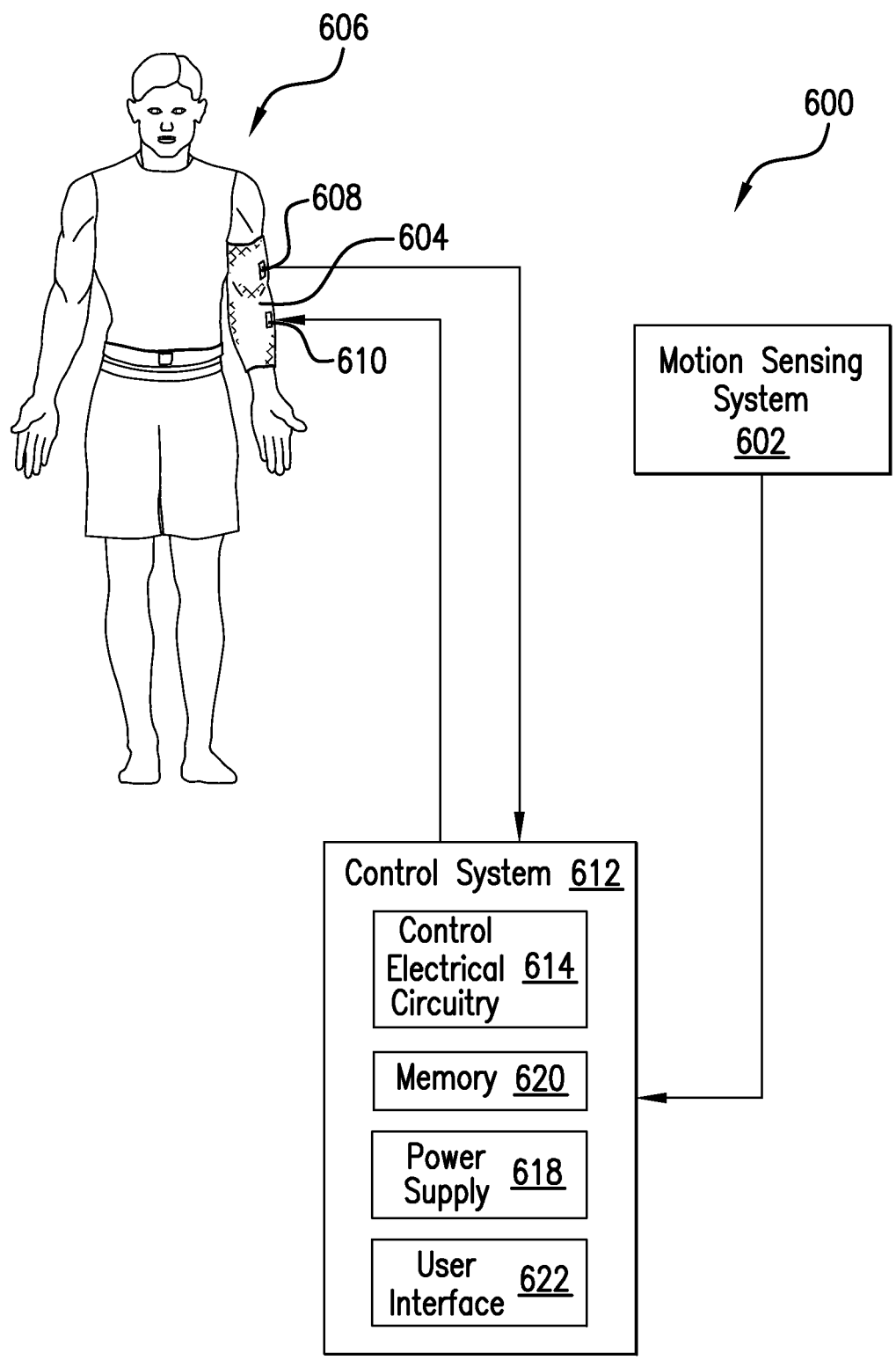
FIG. 6 is a functional block diagram of an embodiment of a garment system including a motion sensing system.

The garment systems disclosed herein can also be used in conjunction with a motion sensing system for teaching or correcting a subject's movement during different activities, such as walking, running, jumping, or specific sporting activities. FIG. 6 is a functional block diagram of an embodiment of a garment system 600 including a motion sensing system 602 and a compression garment 604 configured to be worn by a subject 606. For example, the motion sensing system 602 can be a Microsoft Kinect™ system or a machine vision sensing system that is configured to track physical movement of the subject 606, such as motion of one or more limbs of the subject. For example, such physical movement can be sporting activities, such as a baseball bat swing, golf swing, tennis racquet swing, or other type of activity, or general movement such as walking or arm motion for physical therapy. The compression garment 604 includes one or more activity sensors 608 and one or more actuators 610 shown schematically that can configured as any of the activity sensors and actuators disclosed herein.

The garment system 600 further includes a control system 612 having control electrical circuitry 614 configured to direct the one or more actuators 610 via one or more actuation signals 616 to cause the flexible compression garment 604 to selectively compress against or selectively relieve compression against at least one body part of the subject 606 responsive to receiving one or more sensing signals from the one or more activity sensors 608 and one or more motion signals 609 from the motion sensing system 602. The control system 612 further includes memory 620 operably coupled to the control electrical circuitry 614 that can be programmed with instructions via a user interface 622, and a power supply 618 (e.g., a battery or other suitable power supply) that can power at least some of the components of the garment system 600, such as the control electrical circuitry 614, the one or more activity sensors 608, or the one or more actuators 610.

The memory 620 can be programmed via the user interface 622 so that instructions for the operation of the garment system 600 are stored thereon. For example, the user interface 622 can include a keypad, monitor, touch screen, voice command recognition, or combinations thereof that is operably coupled to the control electrical circuitry 614 of the control system 612. The subject that wears the garment system 600 or another party (e.g., a medical or athletic professional) can program instructions for the operation of the one or more activity sensors 608 or the one or more actuators 610 via the user interface 622.

In operation, responsive to receiving one or more sensing signals from the one or more activity sensors 608 and one or more motion signals 609 from the motion sensing system 602, the control electrical circuitry 614 of the control system 612 directs the one or more actuators 610 to cause the flexible compression garment 604 to selectively compress against or selectively relieve compression against the at least one body part of the subject 606. The selective compression or relief of compression is provided to direct the subject's 606 movement to correspond to a stored movement or movement pattern in the memory 620 of the control system 612. For example, the stored movement or movement pattern can be a model golf swing or other athletic movement as input via the user interface 622 by a golf professional or other athletic professional. The selective compression or relief of compression against the at least one body part (e.g., the subject's 606 arm) is provided to direct the subject's 606 movement to correspond to and substantially follow the movement or movement pattern stored in the memory 620. Thus, the garment system 600 can serve assist training the subject 606 in specific movements for sporting activities, or general movement such as walking for physical therapy. In another embodiment, responsive to receiving the input from the motion sensing system 602 via the one or more motion sensing signals 609, the memory 620 can be programmed with at least one operational program according to which the actuating the one or more actuators 610 occurs.

Figure 7:
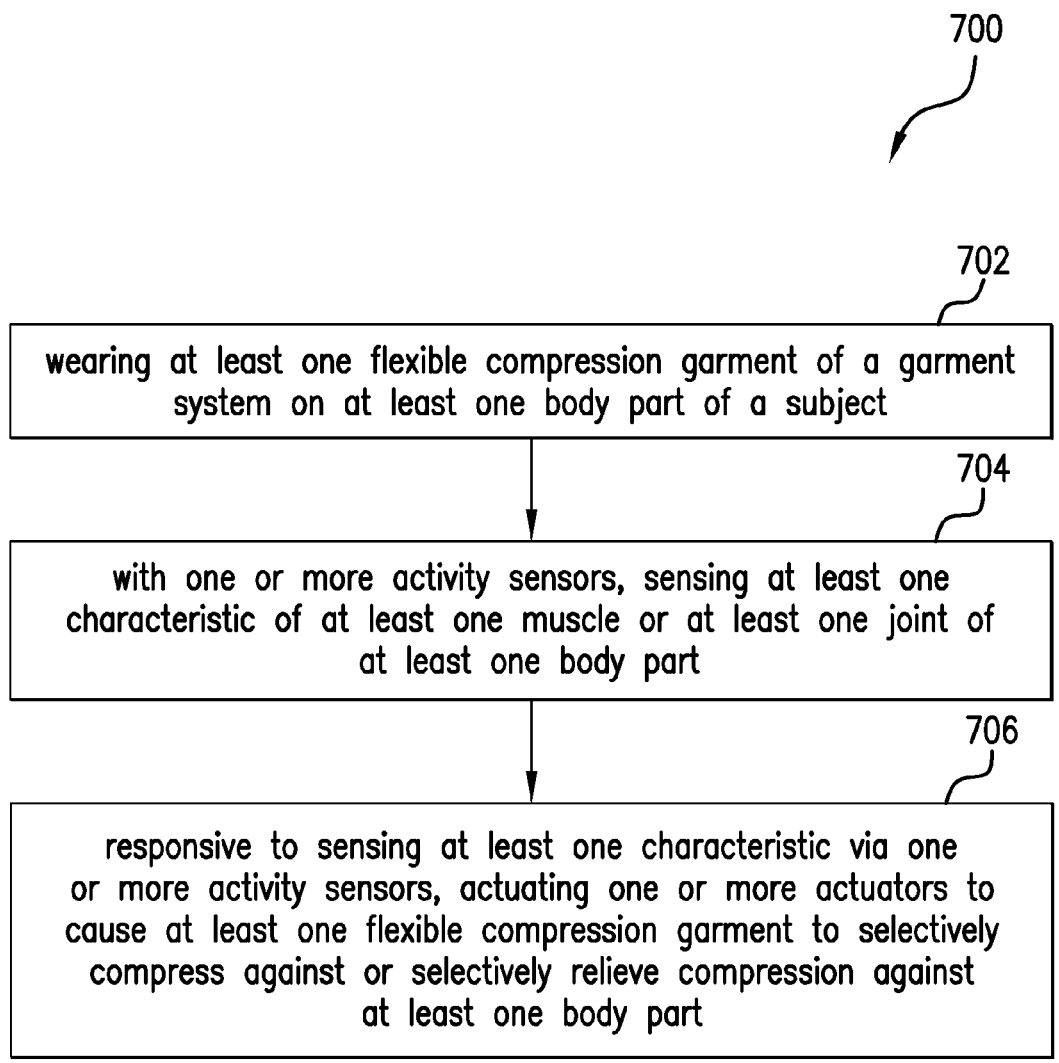
FIG. 7 is a flow diagram of an embodiment of a method of selectively compressing or relieving compression of at least one body part of a subject responsive to sensing feedback from one or more activity sensors.

FIG. 7 is a flow diagram of an embodiment of a method 700 of selectively compressing or relieving compression of at least one body part of a subject responsive to sensing feedback from one or more activity sensors. Instructions for any of the methods disclosed herein can be stored in memory of a garment system such as the memory 512 of the garment system 500.

The method 700 includes an act 702 of wearing at least one flexible compression garment of a garment system on at least one body part of a subject. For example, the at least one body part on which the at least flexible compression garment is worn includes at least a portion of an arm, at least a portion of a forearm, at least a portion of a wrist, at least a portion of a thigh, at least a portion of a lower leg, at least a portion of a neck, or at least a portion of a chest. The garment system includes one or more activity sensors configured to sense at least one characteristic of at least one muscle or at least one joint of the at least body part that is related to muscle activity or joint activity thereof and one or more actuators configured to cause the at least one flexible compression garment to selectively compress against or selectively relieve compression against the at least one body part as disclosed in any of the garment systems disclosed herein, such as the garment system 100 shown in FIG. 1.

The method 700 further includes an act 704 of, with the one or more activity sensors, sensing the at least one characteristic of at least one muscle or at least one joint of the at least one body part. As previously discussed, the at least one characteristic can include at least one of nerve activity of the at least one muscle of the at least one body part, temperature of the at least one muscle or the at least one joint of the at least one body part, oxygenation of the at least one muscle of the at least one body part, acoustic emission from the at least one joint of the at least one body part, or other suitable characteristic that can be correlated to muscle or joint activity. Furthermore, in one or more embodiments, the one more activity sensors can sense only the muscle activity (e.g., one or more muscle activity sensors) or sense only joint activity (e.g., one or more joint activity sensors).

The method 700 also includes an act 706 of, responsive to sensing the at least one characteristic via the one or more activity sensors, actuating the one or more actuators to cause the at least one flexible compression garment to selectively compress against or selectively relieve compression against the at least one body part. For example, in an embodiment, actuating the one or more actuators to cause the at least one flexible compression garment to selectively compress against the at least one body part is responsive to the at least one characteristic sensed by one or more activity sensors being over or below a threshold level, such as indicative of the at least one muscle being injured, exerted, or strained past a strain limit. For example, such a threshold level can be stored in memory of a garment system such as the memory 512 of the garment system 500.

Figure 8:
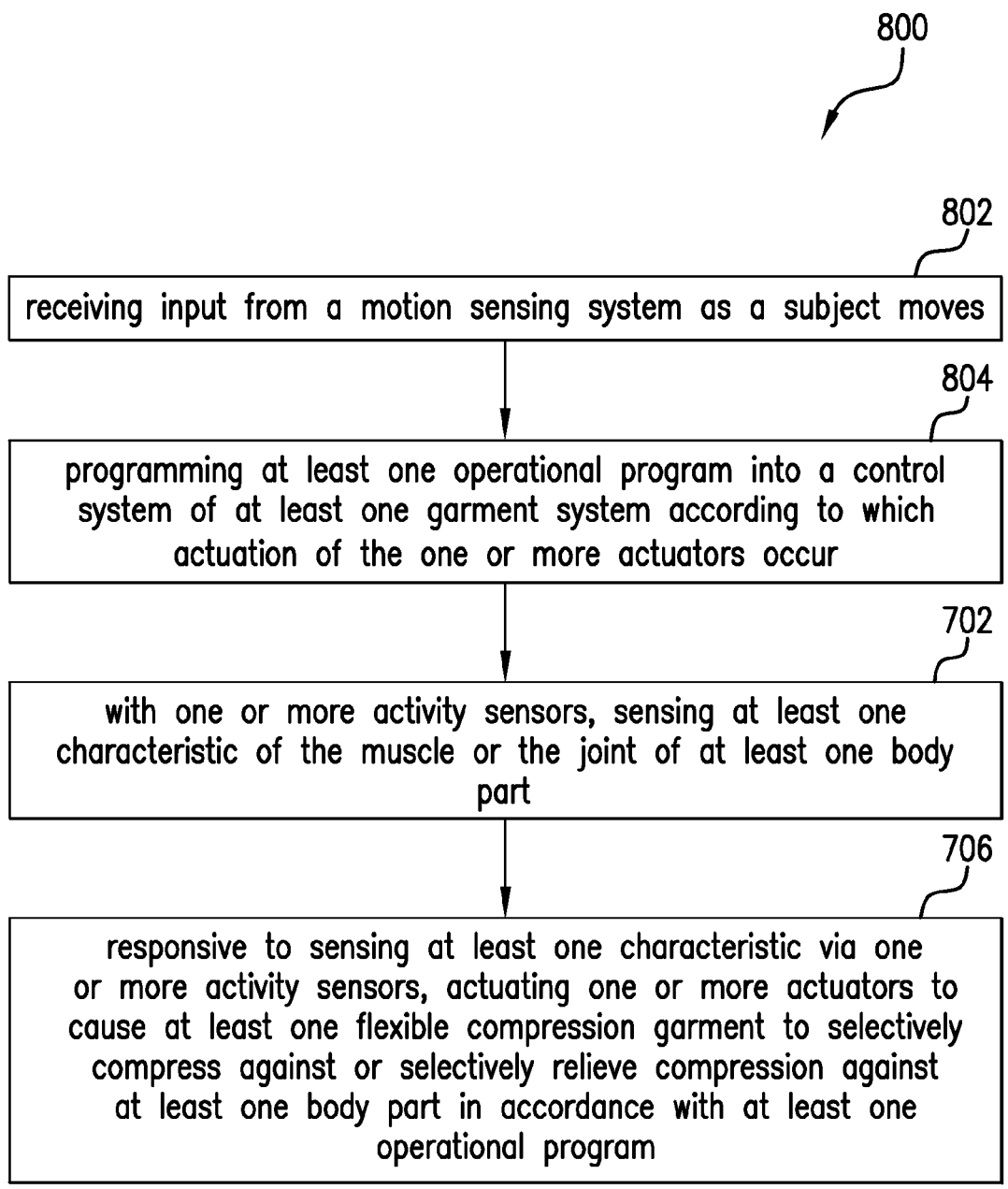
FIG. 8 is a flow diagram of an embodiment of a method in which a garment system receives input from a motion sensing system.

Referring to FIG. 8, an embodiment of a method 800 includes an act 802 of receiving input from a motion sensing system as the subject moves. The method 800 further includes, responsive to receiving the input, an act 804 of programming at least one operational program into a control system of the at least one garment according to which actuation of the one or more actuators occurs.

Thus, in an embodiment, actuating the one or more actuators to cause the at least one flexible compression garment to selectively compress against or selectively relieve compression against the at least one body part occurs according to a pre-programmed at least one operational program. For example, the at least one operational program can be programmed into memory of a control system that controls the one or more actuators, such as the garment system 500 shown in FIG. 5. In an embodiment, the at least one operational program is related to skills training for at least one selected activity, such as strength training, golf, baseball, basketball, handball, tennis, football, billiards, darts, or Frisbee, or physical therapy.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A garment system, comprising:
    at least one flexible compression garment adapted to be worn on at least one body part of a subject, the at least one flexible compression garment defining an interior space adapted to receive the at least one body part;
    one or more activity sensors supported by the at least one flexible compression garment, the one or more activity sensors positioned and configured to sense at least one characteristic of at least one muscle or at least one joint of the at least one body part that is related to muscle activity or joint activity thereof, the one or more activity sensors further configured to output one or more sensing signals indicative of the at least one characteristic;
    one or more actuators positioned relative to the at least one flexible compression garment and configured to cause the at least one flexible compression garment to selectively compress against or selectively relieve compression against the at least one body part; and
    a control system operably coupled to the one or more actuators and further operably coupled to the one or more activity sensors to receive the one or more sensing signals therefrom, the control system including control electrical circuitry configured to direct the one or more actuators to cause the at least one flexible compression garment to selectively compress against or selectively relieve compression against the at least one body part responsive to the one or more sensing signals from the one or more activity sensors.

2. The garment system of claim 1, wherein the at least one characteristic of the at least one muscle of the at least one body part includes at least one of nerve activity of the at least one muscle, temperature of the at least one muscle, oxygenation of the at least one muscle, acoustic emission from the at least one muscle, or biochemical activity of the at least one muscle.

3. The garment system of claim 1, wherein the at least one characteristic of the at least one joint of the at least one body part includes at least one of temperature of the at least one joint, oxygenation of the at least one joint, acoustic emission from the at least one joint, or biochemical activity of the at least one joint.

4. The garment system of claim 1, wherein the one or more activity sensors include at least one of an electromyography sensor, a thermal sensor, a muscle oxygenation sensor, a chemical sensor, or an acoustic sensor.

5. The garment system of claim 1, wherein the one or more activity sensors are configured to sense onset of muscle activity of the at least one muscle, and wherein the control electrical circuitry is configured to direct the one or more actuators to selectively compress against the at least one body part responsive to sensing the onset of muscle activity but prior to the muscle activity occurring.

6. The garment system of claim 5, wherein the one or more activity sensors are configured to sense nerve impulses of the at least one muscle indicative of the onset of the muscle activity.

7. The garment system of claim 6, wherein the one or more activity sensors include an electromyography sensor.

8. The garment system of claim 4, wherein the thermal sensor includes a passive infrared sensor positioned and configured to sense infrared radiation from the at least one muscle of the at least one body part.

9. The garment system of claim 4, wherein the muscle oxygenation sensor includes a passive infrared sensor positioned and configured to sense infrared radiation from the at least one muscle of the at least one body part.

10. The garment system of claim 4, wherein the acoustic sensor includes an acoustic transducer configured to irradiate the at least one muscle or the at least one joint of the at least one body part with acoustic radiation and receive reflected acoustic radiation responsive thereto.

11. The garment system of claim 10, wherein each of the acoustic radiation and the reflected acoustic radiation includes ultrasound radiation.

12. The garment system of claim 4, wherein the acoustic sensor is positioned and configured to sense acoustic emission from the at least one joint of the at least one body part.

13. The garment system of claim 1, wherein the flexible compression garment includes an interior surface defining the interior space, and wherein the one or more activity sensors are disposed at least partially on the interior surface.

14. The garment system of claim 1, wherein the one or more actuators include at least one of one or more electroactive polymer actuators, one or more electroactive metallic actuators, one or more motors, or one or more hydraulic actuators.

15. The garment system of claim 14, wherein the one or more electroactive polymer actuators include one or more actuator elements at least partially formed from ferroelectric polymers, dielectric elastomers, or electrostrictive graft elastomers.

16. The garment system of claim 14, wherein the one or more electroactive metallic actuators include one or more actuator elements at least partially formed from a shape memory material.

17. The garment system of claim 16, wherein the shape memory material includes a nickel-titanium shape memory alloy.

18. The garment system of claim 14, wherein the one or more one or more motors include one or more micro-electromechanical motors.

19. The garment system of claim 1, wherein the one or more actuators extend circumferentially along the at least one flexible compression garment, and are positioned and configured to increase or decrease the interior space of the at least one flexible compression garment responsive to actuation thereof.

20. The garment system of claim 19, wherein the one or more actuators include a plurality of actuators that each extend circumferentially about the at least one flexible compression garment.

21. The garment system of claim 1, wherein the one or more actuators includes a substantially tubular actuator.

22. The garment system of claim 1, wherein the one or more actuators are at least partially embedded within the flexible compression garment.

23. The garment system of claim 1, wherein the flexible compression garment defines an exterior, and wherein the one or more actuators extend about at least a portion of the exterior of the flexible compression garment.

24. The garment system of claim 1, wherein the control system includes:
a power supply operably coupled to the one or more actuators and the control electrical circuitry; and
wherein the control electrical circuitry of the control system is configured to direct the power supply to alter an actuation stimulus to the one or more actuators, which causes actuation thereof, responsive to the one or more sensing signals from the one or more activity sensors.

25. The garment system of claim 24, wherein the one or more actuators include one or more electroactive polymer actuators, and wherein the power supply includes a voltage source configured to apply a voltage to the one or more electroactive polymer actuators to cause actuation thereof.

26. The garment system of claim 24, wherein the one or more actuators include one or more electroactive metallic actuators, and wherein the power supply is configured to apply a current to the one or more electroactive metallic actuators to cause actuation thereof.

27. The garment system of claim 1, wherein the control electrical circuitry of the control system is configured to direct the one or more actuators to apply a gradient of compression along the at least one body part responsive to the one or more sensing signals from the one or more activity sensors.

28. The garment system of claim 1, wherein the control electrical circuitry of the control system is configured to direct the one or more actuators to apply compression pulses to the at least one body part responsive to the one or more sensing signals from the one or more activity sensors.

29. The garment system of claim 1, wherein the control system includes memory configured to store data corresponding to the one or more sensing signals and data corresponding to the selective compression or the selective relief of compression of the at least one flexible compression garment.

30. The garment system of claim 1, wherein the control electrical circuitry of the control system is configured to direct the one or more actuators to cause the at least one flexible compression garment to selectively compress against the at least one body part responsive to the one or more sensing signals from the one or more activity sensors being indicative of the at least one characteristic being below or above a threshold level.

31. The garment system of claim 1, wherein the control electrical circuitry of the control system is configured to direct the one or more actuators to cause the at least one flexible compression garment to selectively compress against the at least one body part responsive to the one or more sensing signals from the one or more activity sensors being indicative of the at least one muscle being strained past a strain limit or injured.

32. The garment system of claim 1, wherein the control electrical circuitry of the control system is configured to direct the one or more actuators to cause the at least one flexible compression garment to selectively compress against the at least one body part responsive to the one or more sensing signals from the one or more activity sensors being indicative of the at least one muscle being exerted.

33. The garment system of claim 1, wherein the control system includes a user interface through which the control system can be programmed with at least one operational program that controls the amount of selective compression applied by the one or more actuators.

34. The garment system of claim 33, wherein the at least one operational program is related to skills training for at least one selected activity.

35. The garment system of claim 34, wherein the at least one selected activity includes at least one of strength training, golf, baseball, basketball, handball, tennis, football, billiards, darts, or Frisbee.

36. A garment system, comprising:
at least one flexible compression garment adapted to be worn on at least one body part of a subject, the at least one flexible compression garment defining an interior space adapted to receive the at least one body part;
one or more muscle activity sensors supported by the at least one flexible compression garment, the one or more muscle activity sensors positioned and configured to sense at least one characteristic of at least one muscle of the at least body part that is related to muscle activity thereof, the one or more muscle activity sensors further configured to output one or more sensing signals indicative of the at least one characteristic;
one or more actuators positioned relative to the at least one flexible compression garment and configured to cause the at least one flexible compression garment to selectively compress against or selectively relieve compression against the at least one body part; and a control system operably coupled to the one or more actuators and further operably coupled to the one or more muscle activity sensors to receive the one or more sensing signals therefrom, the control system including control electrical circuitry configured to direct the one or more actuators to cause the at least one flexible compression garment to selectively compress against the at least one body part responsive to the one or more sensing signals from the one or more muscle activity sensors indicating that the muscle activity is over or below a threshold level.

37. A method, comprising:
wearing at least one flexible compression garment of a garment system on at least one body part of a subject, the garment system including one or more activity sensors configured to sense at least one characteristic of at least one muscle or at least one joint of the at least one body part that is related to muscle activity or joint activity thereof and one or more actuators configured to cause the at least one flexible compression garment to selectively compress against or selectively relieve compression against the at least one body part;
with the one or more activity sensors, sensing the at least one characteristic of the at least one muscle or the at least one joint of the at least one body part; and
responsive to sensing the at least one characteristic via the one or more activity sensors, actuating the one or more actuators to cause the at least one flexible compression garment to selectively compress against or selectively relieve compression against the at least one body part.

38. The method of claim 37, wherein sensing the at least one characteristic of the at least one muscle or the at least one joint of the at least one body part includes sensing only the at least one characteristic of the at least one muscle of the at least one body part.

39. The method of claim 37, wherein sensing the at least one characteristic of the at least one muscle or the at least one joint of the at least one body part includes sensing only the at least one characteristic of the at least one joint of the at least one body part.

40. The method of claim 37, wherein the at least one characteristic of the at least one muscle or the at least one joint of the at least body part includes at least one of nerve activity of the at least one muscle, temperature of the at least one muscle or the at least one joint, oxygenation of the at least one muscle, acoustic emission from the at least one joint, or reflected acoustic radiation from the at least one muscle or the at least one joint.

41. The method of claim 37, wherein sensing the at least one characteristic of the at least one muscle or the at least one joint of the at least one body part includes sensing the at least one characteristic prior to the onset of the muscle activity, wherein the at least one characteristic includes nerve activity of the at least one muscle.

42. The method of claim 37, wherein actuating the one or more actuators to cause the at least one flexible compression garment to selectively compress against or selectively relieve compression against the at least one body part includes applying a voltage or a current to the one or more actuators to cause actuation thereof.

43. The method of claim 37, further including storing, in memory, sensing data from the one or more activity sensors and actuation data corresponding to the selective compression or the selective relief of compression of the at least one flexible compression garment.

44. The method of claim 37, wherein actuating the one or more actuators to cause the at least one flexible compression garment to selectively compress against or selectively relieve compression against the at least one body part is responsive to the at least one characteristic sensed by one or more activity sensors being indicative of the at least one muscle being injured.

45. The method of claim 37, wherein actuating the one or more actuators to cause the at least one flexible compression garment to selectively compress against the at least one body part is responsive to the at least one characteristic sensed by one or more activity sensors being over or below a threshold level.

46. The method of claim 37, wherein actuating the one or more actuators to cause the at least one flexible compression garment to selectively compress against or selectively relieve compression against the at least one body part is responsive to the at least one characteristic sensed by one or more activity sensors being indicative of the at least one muscle being exerted or strained past a strain limit.

47. The method of claim 37, wherein actuating the one or more actuators to cause the at least one flexible compression garment to selectively compress against or selectively relieve compression against the at least one body part occurs according to at least one pre-programmed operational program.

48. The method of claim 47, wherein the at least one operational program is related to skills training for at least one selected activity.

49. The method of claim 37, further including programming at least one operational program into a control system of the at least one garment according to which the actuating the one or more actuators occurs.

50. The method of claim of claim 37, further including:
receiving input from a motion sensing system as the subject moves; and
responsive to receiving the input, programming at least one operational program into a control system of the at least one garment according to which the actuating the one or more actuators occurs.

* * * * *

UNITED STATES PATENT AND TRADEMARK OFFICE
CERTIFICATE OF CORRECTION

PATENT NO. : 9,687,404 B2
APPLICATION NO. : 14/469169
DATED : June 27, 2017
INVENTOR(S) : Cheatham, III et al.

Page 1 of 1

It is certified that error appears in the above-identified patent and that said Letters Patent is hereby corrected as shown below:

In the Claims

Column 23, Claim 18, Lines 23-24:
"wherein the one or more one or more motors..." should read --wherein the one or more motors...--

Column 25, Claim 40, Line 43:
"joint of the at least body part..." should read --joint of the at least one body part...--

Signed and Sealed this
Twenty-ninth Day of May, 2018

Andrei Iancu
*Director of the United States Patent and Trademark Office*